US006342232B1

(12) United States Patent
Loosmore et al.

(10) Patent No.: US 6,342,232 B1
(45) Date of Patent: Jan. 29, 2002

(54) **MULTI-COMPONENT VACCINE COMPRISING AT LEAST THREE ANTIGENS TO PROTECT AGAINST DISEASE CASED BY *HAEMOPHILUS INFLUENZAE***

(75) Inventors: Sheena M. Loosmore, Aurora; Yan-Ping Yang; Michel H. Klein, both of Willowdale, all of (CA)

(73) Assignee: Aventis Pasteur Limited, Toronto (CA)

(*) Notice: Subject to any disclaimer, the term of this patent is extended or adjusted under 35 U.S.C. 154(b) by 0 days.

(21) Appl. No.: 09/261,182

(22) Filed: Mar. 3, 1999

(51) Int. Cl.[7] .............................................. A61K 39/102

(52) U.S. Cl. ............................... 424/256.1; 424/193.1; 424/200.1; 424/201.1; 424/203.1; 424/202.1; 424/282.1; 435/69.1; 530/350

(58) Field of Search .......................... 424/193.2, 200.1, 424/201.1, 202.1, 256.1, 282.1, 163.1, 203.1; 435/69.1, 252.3, 320.1; 536/23.7; 530/350

(56) References Cited

U.S. PATENT DOCUMENTS

| | | | |
|---|---|---|---|
| 4,496,538 | A | 1/1985 | Gordon |
| 5,506,139 | A | 4/1996 | Loosmore et al. |
| 5,603,938 | A | 2/1997 | Barenkamp |
| 5,646,259 | A | 7/1997 | St. Geme, III et al. |
| 5,869,302 | A | 2/1999 | Loosmore |

FOREIGN PATENT DOCUMENTS

| | | |
|---|---|---|
| WO | WO 94/00149 | 1/1994 |
| WO | WO 94/21290 | 9/1994 |
| WO | WO 95/34308 | 12/1995 |
| WO | 97/36914 | * 10/1997 |
| WO | WO 00/35477 | 6/2000 |

OTHER PUBLICATIONS

Barbour, M.L., R.T. Mayon–White, C. Coles, D.W.M. Crook, and E.R. Moxon. 1995. The impact of conjugate vaccine on carriage of *Haemophilus influenzae* type b. J. Infect. Dis. 171:93–98.

Berkowitz et al. 1987. J. Pediatr. 110:509.

Claesson et al. 1989. J. Pediatr. 114:97.

Black, S.B., H.R., Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.

Nitta, D.M., M.A. Jackson, V.F. Burry, and L.C. Olson. 1995. Invasive *Haemophilus Influenzae* type f disease. Pediatr. Infect. Dis. J. 14:157–160.

Waggoner–Fountain, L.A., J.O. Hendley, E.J. Cody, V.A. Perriello, and L.G. Donowitz. 1995. The emergence of *Haemophilus influenzae* types e and f as significant pathogens. Clin. Infect. Dis. 21:1322–1324.

Madore, D.V. 1996. Impact of immunization on *Haemophilus influenzae* type b disease. Infectious Agents and Disease 5:8–20.

Bluestone, C.D. 1982. Current concepts in otoloaryngology. Otitis media in children: to treat or not to treat? N. Engl. J. Med. 306:1399–1404.

Barenkamp, S.J., and F.F. Bodor. 1990. Development of serum bactericida activity followingnon–typable *Haemophilus influenzae* acute otitis media. Pediatr. Infect. Dis. 9:333–339.

Barenkamp, S.J., and J.W. St. Geme III. 1994. Genes encoding high–moleular weight adhesion proteins of non–typeable *Haemophilus influenzae* are part of gene clusters. Infect. Immun. 62:3320–3328.

St. Geme III J.W., V.V. Kumar, D. Cutter, and S.J. Barenkamp. 1998. Prevalence and distribution of the hmw and hia genes and the HMW and Hia adhesins among genetically diverse strains of non–typeable *Haemophilus influenzae.* Infect. Immun. 66:364–368.

St. Geme III, J. W., S. Falkow, and S.J. Barenkamp. 1993. High–molecular–weight proteins of non–typeable *Haemophilus influenzae* mediate attachment to human epithelial cells. Proc. Natl. Acad. Sci. USA 90 :2875–2879.

Barenkamp, S.J. 1996. Immunization with high–molecular–weight adhesion proteins of non–typeable *Haemophilus influenzae* modifies experimental otitis media in chinchillas. Infect. Immun. 64:1246–1251.

Yang, Y.P., S.M. Loosmore, B. Underdown, and M.H. Klein, 1998. Nasopharyngeal colonization with non–typeable *H. influenzae*, in chinchillas. Infect. Immun. 66:1973–1980.

St. Geme, J.W. and D. Cutter. 1995. Evidence that surface fibrils expressed by *Haemophilus influenzae* type b promote attachment to human eptihelial cells. Molec. Microbiol. 15:77–85.

Barenkamp, S.J. and J.W. St. Geme. 1996. Identification of a second family of high–molecular–weight adhesion proteins expressed by non–typeable *Haemophilus influenzae.* Molec. Microbiol. 19:1215–1223.

(List continued on next page.)

*Primary Examiner*—Jennifer E. Graser
(74) *Attorney, Agent, or Firm*—Sim & McBurney

(57) ABSTRACT

A multi-component immunogenic composition confers protection on an immunized host against infection caused by *Haemophilus influenzae*. Such composition comprises at least three different antigens of *Haemophilus influenzae*, two of which are adhesins. High molecular weight (HMW) proteins and *Haemophilus influenzae* adhesin (Hia) proteins of non-typeable *Haemophilus influenzae* comprise the adhesin components while the other antigen is a non-proteolytic analog of Hin47 protein. Each component does not impair the immunogenicity of the others. The Haemophilus vaccine may be combined with DTP component vaccines, which may contain inactivated poliovirus, including type 1, type 2 and/or type 3, and/or a conjugate of a capsular polysaccharide of *Haemophilus influenzae* and tetanus or diphtheria toxoid, including PRP-T, to provide a multi-valent component vaccine without impairment of the immunogenic properties of the other antigens.

20 Claims, 19 Drawing Sheets

OTHER PUBLICATIONS

St. Geme, J.W., D. Cutter and S.J. Barenkamp. 1996. Characterization of the genetic locus encoding *Haemophilus influenzae* type be surface fibril. J. Bact. 178:6281–6287.
Retzlaff, C., Y. Yamamoto, P.S. Hoffman, H Friedman, and T.W. Klei.,1994. Bacterial heat shock proteins directly induce cytokine MRNA and interleukin–1 secretion in macrophage cultures. Infect. Immun. 62:5689–5693.
Loosmore, S.M., Y–P. Yang, R. Oomen, J.M. Shortreed, D.C. Coleman, and M.H. Klein. 1998. The *Haemophilus influenzae* HtrA protein is a protective antigen. Infect. Immun. 66:899–906.
Tabor S. and Richardson C.C., 1985. A. bacteriophage T7 RNA polymerase/promoter system for controlled exclusive expression of specific genes. Proc. Natl. Acad. Sci. 82(4): 1074–1078.
Holmes, D.S. and Quigley, M. 1981. A rapid boiling method for the preparation of bacterial plasmids. Anal. Biochem. 114:193–197.

* cited by examiner

*pT7hmw1ABC (125)/cer/KanR*

Oligonucleotides used to PCR amplify the full-length strain 11 hia gene for expression studies.

sense

```
          EcoR I Nde I
            ↓      ↓
                     M  N  K  I  F  N  V  I  W  N                        SEQ ID no: 2
5'    GCGAATTCATATGAACAAAATTTTTAACGTTATTTGGAAT  3'         5038.SL   SEQ ID no: 3
```

antisense

```
       K  T  G  V  A  A  G  V  G  Y  Q  W  *  *                                      SEQ ID no: 4
5'    AAAACAGGCGTTGCAGCAGGTGTTGGTTACCAGTGGTAATAG                3'               SEQ ID no: 5
3'    TTTTGTCCGCAACGTCGTCCACAACCAATGGTCACCATTATCTTAAGGCCTAGGCG  5'    5039.SL   SEQ ID no: 6
                                                ↑       ↑
                                             EcoR I  BamH I
```

FIG.11

Oligonucleotides primers to PCR amplify truncated V38 strain 11 hia gene

V38

```
                 M  V  L  A  T  L  L  S  A  T                               SEQ ID no: 7
5'   GGGAATTCATATGGTATTGGCAACCCTGTTGTCCGCAACG          3'     5526.SL      SEQ ID no: 8
```

antisense

```
      H  T  I  T  F  A  L  A  K  D  L  G                                    SEQ ID no: 9
5'    CACACCATTACCTTTGCGCTAGCGAAAGACCTTGGTGG           3'                  SEQ ID no: 10
3'    GTGTGGTAATGGAAACGCGATCGCTTTCTGGAACCACCCTAGGGC    5'     5528.SL      SEQ ID no: 11
                            ↑               ↑      ↑
                          Nhe I           Sty I  BamH I
```

FIG.12

SEQUENCE LISTING

<160> NUMBER OF SEQ ID NOS: 11

<210> SEQ ID NO 1
<211> LENGTH: 21
<212> TYPE: DNA
<213> ORGANISM: Haemophilus influenzae

<400> SEQUENCE: 1
atcaataaca gcattattgg t 21

<210> SEQ ID NO 2
<211> LENGTH: 10
<212> TYPE: PRT
<213> ORGANISM: Haemophilus influenzae

<400> SEQUENCE: 2

Met Asn Lys Ile Phe Asn Val Ile Trp Asn
1 5 10

<210> SEQ ID NO 3
<211> LENGTH: 40
<212> TYPE: DNA
<213> ORGANISM: Haemophilus influenzae

<400> SEQUENCE: 3
gcgaattcat atgaacaaaa tttttaacgt tatttggaat 40

<210> SEQ ID NO 4
<211> LENGTH: 12
<212> TYPE: PRT
<213> ORGANISM: Haemophilus influenzae

<400> SEQUENCE: 4

Lys Thr Gly Val Ala Ala Gly Val Gly Tyr Gln Trp
1 5 10

<210> SEQ ID NO 5
<211> LENGTH: 42
<212> TYPE: DNA
<213> ORGANISM: Haemophilus influenzae

<400> SEQUENCE: 5
aaaacaggcg ttgcagcagg tgttggttac cagtggtaat ag 42

<210> SEQ ID NO 6
<211> LENGTH: 56
<212> TYPE: DNA
<213> ORGANISM: Haemophilus influenzae

<400> SEQUENCE: 6
gcggatccgg aattctatta ccactggtaa ccaacacctg ctgcaacgcc tgtttt 56

<210> SEQ ID NO 7
<211> LENGTH: 10
<212> TYPE: PRT
<213> ORGANISM: Haemophilus influenzae

<400> SEQUENCE: 7

Met Val Leu Ala Thr Leu Leu Ser Ala Thr
1 5 10

<210> SEQ ID NO 8

-continued

<211> LENGTH: 40
<212> TYPE: DNA
<213> ORGANISM: Haemophilus influenzae

<400> SEQUENCE: 8
gggaattcat atggtattgg caaccctgtt gtccgcaacg 40

<210> SEQ ID NO 9
<211> LENGTH: 12
<212> TYPE: PRT
<213> ORGANISM: Haemophilus influenzae

<400> SEQUENCE: 9

His Thr Ile Thr Phe Ala Leu Ala Lys Asp Leu Gly
1 5 10

<210> SEQ ID NO 10
<211> LENGTH: 38
<212> TYPE: DNA
<213> ORGANISM: Haemophilus influenzae

<400> SEQUENCE: 10
cacaccatta cctttgcgct agcgaaagac cttggtgg 38

<210> SEQ ID NO 11
<211> LENGTH: 45
<212> TYPE: DNA
<213> ORGANISM: Haemophilus influenzae

<400> SEQUENCE: 11
cgggatccca ccaaggtctt tcgctagcgc aaaggtaatg gtgtg 45

MULTI-COMPONENT VACCINE COMPRISING AT LEAST THREE ANTIGENS TO PROTECT AGAINST DISEASE CASED BY *HAEMOPHILUS INFLUENZAE*

FIELD OF INVENTION

The present invention relates to the field of vaccinology and, in particular, to a multi-component vaccine comprising recombinant proteins from *Haemophilus influenzae* which is useful in protecting against disease caused by *Haemophilus influenzae* including otitis media.

BACKGROUND OF THE INVENTION

*Haemophilus influenzae* is the cause of several serious human diseases such as meningitis, epiglottitis, septicemia and otitis media. There are six serotypes of *H. influenzae*, designated a to f, that are identified by their capsular polysaccharide. *H. influenzae* type b (Hib) was a major cause of bacterial meningitis until the introduction of several Hib conjugate vaccines in the 1980's (ref. 1, throughout this application, various references are referred to in parenthesis to more fully describe the state of the art to which this invention pertains Full bibliographic information for each citation is found at the end of the specification immediately preceding the claims. The disclosures of these references are hereby incorporated by reference into the present disclosure). Vaccines based upon *H. influenzae* type b capsular polysaccharide conjugated to diphtheria toxoid (ref. 2), tetanus toxoid (ref. 3 and U.S. Pat. No. 4,496,538), or *Neisseria meningitidis* outer membrane protein (ref. 4) have been effective in reducing *H. influenzae* type b-induced meningitis. The other serotypes of *H. influenzae* are associated with invasive disease at low frequencies, although there appears to be an increase in the incidence in disease caused by these strains as the incidence of Hib disease declines (refs. 5 and 6). Non-encapsulated or nontypeable *H. influenzae* (NTHi) are also responsible for a wide range of human diseases including otitis media, epiglottitis, pneumonia and tracheobronchitis. The incidence of NTHi-induced disease has not been affected by the introduction of the Hib vaccines (ref. 7).

Otitis media is the most common illness of early childhood, with 60 to 70% of all children, of less than 2 years of age, experiencing between one and three ear infections (ref. 8). Chronic otitis media is responsible for hearing, speech and cognitive impairments in children. *H. influenzae* infections account for about 30% of the cases of acute otitis media and about 60% of chronic otitis media. In the United States alone, treatment of otitis media costs between 1 and 2 billion dollars per year for antibiotics and surgical procedures, such as tonsillectomies, adenoidectomies and insertion of tympanostomy tubes. It is estimated that an additional $30 billion is spent per annum on adjunct therapies, such as speech therapy and special education classes. Furthermore, many of the causative organisms of otitis media are becoming resistant to antibiotic treatment. An effective prophylactic vaccine against otitis media is thus desirable.

During natural infection, surface-exposed outer membrane proteins that stimulate an antibody response are potentially important targets for bactericidal and/or protective antibodies and therefore potential vaccine candidates. Barenkamp and Bodor (ref. 9) demonstrated that convalescent sera from children suffering from otitis media due to NTHi, contained antibodies to high molecular weight (HMW) proteins. About 70 to 75% of NTHi strains express the HMW proteins and most of these strains contain two gene clusters termed hmw1ABC and hmw2ABC (refs. 10, 11). The HMWA proteins have been demonstrated to be adhesins mediating attachment to human epithelial cells (ref. 12). Immunization with a mixture of native HMW1A and HMW2A proteins resulted in partial protection in the chinchilla intrabulla challenge model of otitis media (ref. 13)

U.S. Pat. No. 5,603,938 (Barenkamp), assigned to St. Louis University and Washington University and the disclosure of which is incorporated herein by reference, describes the cloning, expression and sequencing of the genes encoding the HMW1 and HMW2 proteins from strain 12 of non-typeable *Haemophilus influenzae*. The HMW proteins are a family of proteins from non-typeable *Haemophilus influenzae* of molecular weight of about 120 to 125 kDa which are absent from encapsulated strains of *Haemophilus influenzae*.

The production of native HMW proteins from *H. influenzae* strains is very low and a method for producing protective recombinant HMW (rHMW) proteins has been described in copending U.S. patent application Ser. No. 09/167,568 filed Oct. 7, 1998, assigned to the assignee hereof and the disclosure of which is incorporated herein by reference. A chinchilla nasopharyngeal colonization model has been developed specifically to demonstrate vaccine efficacy of adhesins (ref. 14) and the rHMW proteins are protective in this model as described in the aforementioned copending U.S. patent application Ser. No. 09/167,568. The rHMW1A and rHMW2A proteins were shown to afford equivalent protection and the rHMW1A protein was chosen for further vaccine studies. In this application, rHMW refers to recombinant HMW1A from NTHi strain 12, although other corresponding recombinant HMW1A proteins from other NTHi strains and corresponding HMW2A proteins from NTHi strains may be employed. The corresponding naturally-occurring proteins may be employed.

A second family of high molecular weight adhesion proteins has been identified in about 25% of NTHI and in encapsulated *H. influenzae* strains (refs. 15, 16, 17). The NTHi member of this second family is termed *Haemophilus influenzae* adhesin or Hia and the homologous protein found in encapsulated strains is termed *Haemophilus influenzae* surface fibril protein or Hsf.

U.S. Pat. No. 5,646,259 (St. Geme, III et al), assigned to St. Louis University and Washington University, and the disclosure of which is incorporated herein by reference, describes the cloning, expression and sequences of genes encoding the Hia and Hsf proteins, which have limited homology to the HMW1 and HMW2 proteins of U.S. Pat. No. 5,603,938.

The hia gene was originally cloned from an expression library using convalescent sera from an otitis media patient, which indicates that it is an important immunogen during disease. The prototype Hia and Hsf proteins demonstrate about 82% sequence similarity, although the Hsf protein is considerably larger. The proteins are comprised of conserved amino and carboxy termini and several repeat motifs, with Hsf containing more repeat sequences than Hia.

United States patent application Ser. No. 09/268,347 filed Mar. 26, 1999, assigned to the assignee hereof and the disclosure of which is incorporated herein by reference, describes the production of full-length and N-terminal truncated versions of the Hia protein (rHia) in *E. coli*. These recombinant proteins have been demonstrated to protect against bacteremia caused by *H. influenzae* type a and type b organisms, and to confer partial protection against nasopharyngeal colonization by non-typeable *H. influenzae*. In this application, rHia refers to V38 rHia from NTHi strain 11, although other recombinant full-length and N-terminal truncated Hia proteins from other NTHi strains may be employed. The corresponding naturally-occurring proteins may be employed. The corresponding naturally-occurring proteins may be employed.

When under environmental stress, such as high temperature, organisms overproduce stress response or heat shock proteins (hsps). Bacterial hsps have been shown to be important immunogens, stimulating both B cells and T cells (ref. 18). The bacterial HtrA or DegP heat shock proteins are expressed under conditions of stress and the *H. influenzae* HtrA or Hin47 protein has been shown to be a partially protective antigen in the intrabulla challenge model of otitis media (ref. 19). The HtrA proteins are serine proteases and their proteolytic activity makes them unstable. In addition, as components of a multicomponent vaccine, the wild-type HtrA protein will degrade mixed antigens. The site-directed mutagenesis of the *H. influenzae* htrA gene (termed hin47) and the properties of the mutants have been fully described in U.S. Pat. No. 5,506,159 (Loosmore et al), assigned to the assignee hereof and the disclosure of which is incorporated herein by reference.

U.S. Pat. No. 5,506,139 (Loosmore et al) describes the preparation of analogs of *Haemophilus influenzae* Hin47 protein which have a decreased protease activity which is less than about 10% of that of the natural Hin47 protein and which preferably have substantially the same immunogenic properties as natural Hin47 protein. The patent also describes the isolation, purification and characterization of nucleic acid molecules encoding the Hin47 analogs. The natural Hin47 protein is immunologically conserved among non-typeable and type b isolates of *H. influenzae*. The amino acid sequence of the natural Hin47 protein and the nucleotide sequence of the encoding hin47 gene are described in WO 94/00149 published Jan. 6, 1994 and incorporated herein by reference.

The Hin47 analogs of U.S. Pat. No. 5,506,139 are prepared by deleting or replacing by a different amino acid at least one amino acid of the natural Hin47 contributing to protease activity or by inserting at least one amino acid into the natural Hin47 protein, as specifically described therein. The at least one deleted or replaced amino acid may be selected from amino acids 195 to 201 of Hin47 and specifically may be Serine-197, which may be deleted or replaced by alanine. In addition, the at least one deleted or replaced amino acid may be His-91 and may be deleted or replaced by alanine, lysine or arginine. Furthermore the at least one deleted or replaced amino acid may be Asp-121 and may be deleted or replaced by alanine.

In U.S. patent application Ser. No. 08/487,167 filed Jun. 7, 1995, assigned to the assignee hereof and the disclosure of which is incorporated herein by reference (now U.S. Pat. No. 5,869,302), there are described multiple mutations effected at different amino acids of the natural Hin47 protein to provide the non-proteolytic Hin47 analog.

In the present invention, the mutation of histidine 91 to alanine (sometimes termed herein "H91A") is employed as illustration of the mutant Hin47 protein, although other Hin47 mutants with reduced protease activity as described in the aforementioned patent and application may be used.

The non-proteolytic HtrA analogue H91A Hin47, has been shown to be a protective antigen against bacteremia caused by *H. influenzae* type b and against otitis media caused by non-typeable *H. influenzae* (ref. 19). HtrA was found in all strains examined, including all encapsulated strains of *H. influenzae*.

The main goal of a prophylactic vaccine against otitis media is to prevent the establishment of nasopharyngeal colonization by including adhesins as immunogens. The *H. influenzae* HMW and Hia proteins are adhesins that have been shown to prevent colonization. However, since there may be a small percentage of *H. influenzae* strains that do not contain the hmw or hia genes and a wide spectrum of disease protection is desired, the H91A Hin47 antigen has been added to provide protection against such strains, although any other non-proteolytic analogs of Hin47 may be employed. The present invention provides for a multi-component vaccine to protect against colonization and disease caused by encapsulated or non-encapsulated *H. influenzae* organisms.

It would be desirable to provide efficacious combination vaccines comprising *H. influenzae* components containing selected relative amounts of selected antigens.

SUMMARY OF THE INVENTION

The present invention is directed towards the provision of a multi-component vaccine comprising at least three antigens, to protect against disease caused by infection with *Haemophilus influenzae*, including otitis media.

In accordance with one aspect of the present invention, there is provided an immunogenic composition for conferring protection in a host against disease caused by infection by *Haemophilus influenzae*, including otitis media, comprising at least three different antigens of *Haemophilus influenzae*, at least two of which different antigens are adhesins.

One of the antigens which is an adhesin may be a high molecular weight protein (HMW) of a non-typeable strain of Haemophilus, particularly an HMW1 or HMW2 protein of the non-typeable strain, which may be produced recombinantly.

The other of the antigens which is an adhesin is a *Haemophilus influenzae* adhesin (Hia) protein of a non-typeable strain of *Haemophilus influenzae* or a *Haemophilus influenzae* surface fibril (Hsf) protein of a typeable strain of *Haemophilus influenzae*.

The antigen of *Haemophilus influenzae* which is not an adhesin may be a non-proteolytic heat shock protein of a strain of *Haemophilus influenzae*. The non-proteolytic heat shock protein of a strain of *Haemophilus influenzae* may be an analog of *Haemophilus influenzae* Hin47 protein having a decreased protease activity which is less than about 10% of that of the natural Hin47 protein.

In accordance with a preferred embodiment of the aspect of the invention, there is provided an immunogenic composition for conferring protection in a host against disease caused by *Haemophilus influenzae*, including otitis media, which comprises:

(a) an analog of *Haemophilus influenzae* Hin47 protein having a decreased protease activity which is less than about 10% of natural Hin47 protein, (b) a *Haemophilus influenzae* adhesin (Hia) protein of a non-typeable strain of *Haemophilus influenzae*, and (c) a high molecular weight (HMW) protein of a strain of non-typeable *Haemophilus influenzae*.

The analog of Hin47 protein may be one in which at least one amino acid of the natural Hin47 protein contributing to protease activity has been deleted or replaced by a different amino acid and which has substantially the same immunogenic properties as natural Hin47 protein.

Such at least one amino acid may be selected from the group consisting of amino acids 91, 121 and 195 to 207 of natural Hin47 protein. Specific mutants which may be used including serine-197 replaced by alanine, Histidine-91 replaced by alanine, lysine or arginine and Asp-121 replaced by alanine.

The HMW protein of the non-typeable strain of *Haemophilus influenzae* may be a HMW1 or HMW2 protein and may be recombinantly produced. The HMW1 and HMW2 proteins are derived from the respective strains of non-typeable *Haemophilus influenzae* and possess respective molecular weights as set forth in the following Table I:

TABLE I

| | | Non-typeable *H. influenzae* Strain | | | | | |
|---|---|---|---|---|---|---|---|
| Molecular Weight (kDa) | | 12 | JoyC | K21 | LCDC2 | PMH1 | 15 |
| Mature Protein: | HMW1 | 125 | 125.9 | 104.4 | 114.0 | 102.4 | 103.5 |
| | HMW2 | 120 | 400.9 | | 111.7 | 103.9 | 121.9 |

The Hia protein may be produced recombinantly and may comprise the N-terminal truncated V38 rHia protein.

The immunogenic composition of the invention may be further formulated with an adjuvant. Such adjuvant for use in the present invention may include (but not limited to) aluminum phosphate, aluminum hydroxide, QS21, Quil A, derivatives and components thereof, ISCOM matrix, calcium phosphate, calcium hydroxide, zinc hydroxide, a glycolipid analog, an octadecyl ester of an amino acid, a muramyl dipeptide, polyphosphazene, ISCOPREP, DC-chol, DDBA and a lipoprotein and other adjuvants. Advantageous combinations of adjuvants are described in copending U.S. patent applications Ser. No. 08/261,194 filed Jun. 16, 1994 and 08/483,856 filed Jun. 7, 1995, assigned to the assignee hereof and the disclosures of which are incorporated herein by reference (WO 95/34308, published Nov. 21, 1995). The adjuvant preferably may comprise aluminum phosphate or aluminum hydroxide (collectively known as alum).

The components of the immunogenic composition may be present in appropriate quantities to provide the desired immune response. The components may be formulated as a vaccine for in vivo administration to the host. The vaccine composition may contain:

(a) about 25 to 100 $\mu$g of the Hin47 protien, (b) about 25 to 100 $\mu$g of the Hia protien, and (c) about 25 to 100 $\mu$g of the HMW protien.

The immunogenic compositions may be formulated with other antigenic components to provide a multivalent vaccine in which the additional antigenic component(s) confer protection against disease caused by another pathogen(s). Such additional antigens should be such that and be present in quantities that the immunogenicity of the individual components of the resulting vaccine is not impaired by other individual components of the composition. Such additional antigens preferably are purified antigens in defined quantities to produce a component vaccine.

Such additional antigens may be those traditionally found in multivalent protective vaccines, such as diphtheria toxoid, tetanus toxoid and pertussis antigens, including pertussis toxoid, filamentous hemagglutinin, pertactin and/or agglutinogens.

The resulting multivalent vaccine also may contain non-virulent poliovirus, such as inactivated poliovirus, which may be type 1, type 2 and/or type 3 poliovirus. The multi-component vaccine further may comprise a conjugate of a tetanus or diphtheria toxoid and a capsular polysaccharide of *Haemophilus influenzae*, preferably PRP-T.

The invention extends to a method of immunizing a host against disease caused by infection by *Haemophilus influenzae*, including otitis media, which comprises administering to the host an immunoeffective amount of the immunogenic composition provided herein.

Advantages of the present invention include a multi-component vaccine that can confer protection against encapsulated and non-encapsulated *Haemophilus influenzae* diseases in a safe and efficacious manner.

BRIEF DESCRIPTION OF DRAWINGS

The present invention will be further understood from the following description with reference to the drawings, in which:

FIG. 11 shows the oligonucleotides used to PCR amplify the strain 11 hia gene. Sense (5038.SL), SEQ ID NO: 2, encoded amino acids SEQ ID NO: 3; Antisense (5039.SL), SEQ ID NO: 4, complement SEQ ID NO: 5, encoded amino acids SEQ ID NO: 6;

FIG. 12 shows the oligonucleotides used to PCR amplify the 5'-fragments to produce the truncated gene. V38 truncation: Sense (5526.SL) : SEQ ID NO: 7, encoded amino acids SEQ ID NO: 8; Anti-sense (5528.SL) SEQ ID NO: 9; complement SEQ ID NO: 10, encoded amino acids SEQ ID NO: 11.

GENERAL DESCRIPTION OF THE INVENTION

Figure 1A:
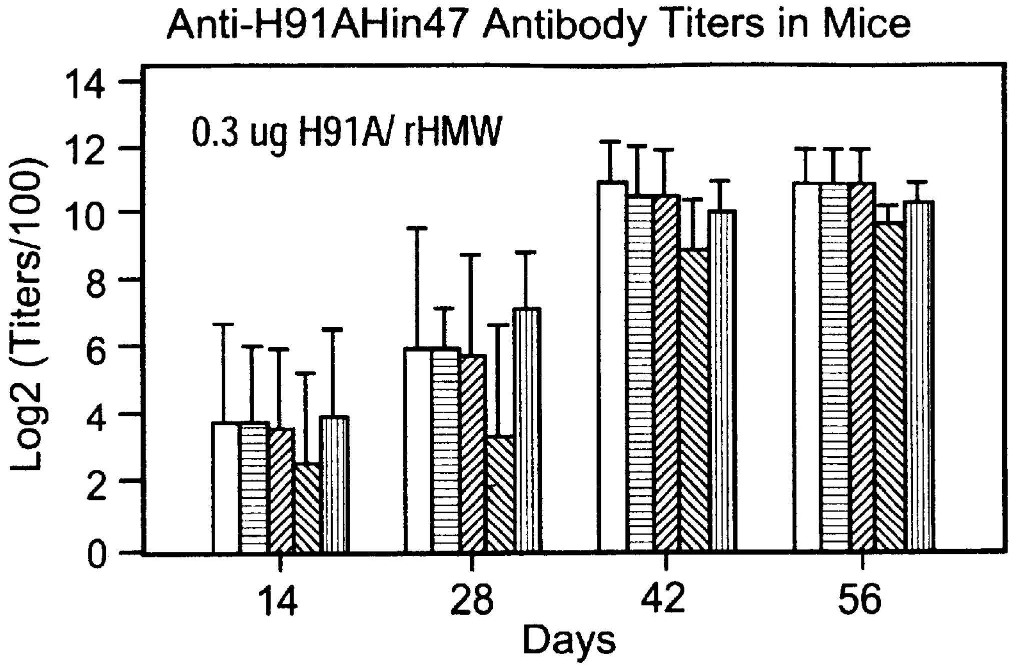
FIG. 1 contains bar graphs A and B, illustrating the anti-H91A Hin47 immune responses for H91A Hin47+rHMW+rHia combination vaccines in mice. Panel A, 0.3 $\mu$g each of H91A Hin47+rHMW and increasing amounts of rHia. Panel B, 3.0 $\mu$g each of H91A Hin47+rHMW and increasing amounts of rHia.

The production and purification of recombinant *H. influenzae* antigens rHMW, rHia and H91A Hin47 have been fully described in the aforementioned U.S. patent applications Ser. Nos. 09/167,568, 09/368,347 and the aforementioned U.S. Pat. No. 5,506,159, respectively.

Colonization of the nasopharynx is the first step in disease development for many bacterial or viral pathogens and vaccines containing adhesin molecules should protect against this first step in disease progression. The high molecular weight (HMW) proteins, found in approximately 75% of non-typeable *H. influenzae*, have been shown to be adhesins that are protective against colonization when administered in a vaccine composition. The HMW proteins are not present in encapsulated *H. influenzae* strains or in about 25% of non-typeable *H. influenzae* strains, thus they are not sufficient for a fully-effective vaccine having strain-wide protectivity.

The Hia/Hsf proteins also have been shown to be adhesins and are present in all encapsulated *H. influenzae* strains and in most of those non-typeable *H. influenzae* strains which do not produce HMW proteins. The rHia protein is protective against colonization by NTHi and against bacteremia caused by *H. influenzae* type a and type b organisms. There is a small percentage of NTHi strains that produce neither HMW nor Hia proteins.

The HtrA protein or Hin47 is found in all encapsulated and non-typeable *H. influenzae* strains. Hin47, or its non-proteolytic H91A Hin47 mutant, is protective against bacteremia caused by *H. influenzae* type b and otitis media caused by non-typeable *H. influenzae*, but it does not prevent colonization. A combination vaccine comprising rHMW, rHia and H91A Hin47 antigens may be formulated to protect against *H. influenzae* disease, including otitis media. Such combination is provided herein.

The composition of multi-component vaccines is critical for maximum efficiency. The vaccine components must be compatible and they must be combined in appropriate ratios to avoid antigenic interference and optimize any possible synergies. If administered with other established vaccines, they must not interfere with the protection afforded by the vaccine against other disease(s).

The preparation, immunogenic and protective properties of a two-component rHMW+H91A Hin47 vaccine have been described in U.S. patent application Ser. No. 09/210,995 filed Dec. 15, 1998, assigned to the assignee hereof and the disclosure of which is incorporated herein by reference.

Various antigen ratios were compared for the three component H91A Hin47+rHMW+rHia vaccine, in two animal species. There was no affect on the anti-H91A Hin47 response with increasing amounts of rHia. Antigenic interference was observed in mice for the anti-rHMW response, when a 0.3 μg dose of each of H91A Hin47+rHMW was mixed with increasing doses of rHia. However, at a 3.0 μg dose of each of H91A Hin47+rHMW, there was no suppression of the anti-rHMW response with increasing amounts of rHia. Although there was a transient suppression of the anti-Hia response on day 42 when a 0.3 μg dose was combined with 3 μg each of H91A+rHMW, this effect was not significant by day 56. In guinea pigs, the anti-H91A Hin47 and anti-rHMW responses were not effected by the addition of rHia. However, there appeared to be a small, but statistical, effect on the anti-Hia response in the presence of H91A Hin47+rHMW for the booster immunizations. These data indicate that the composition of the three component vaccine is critical to achieve a good immune response to all components.

Figure 1B:
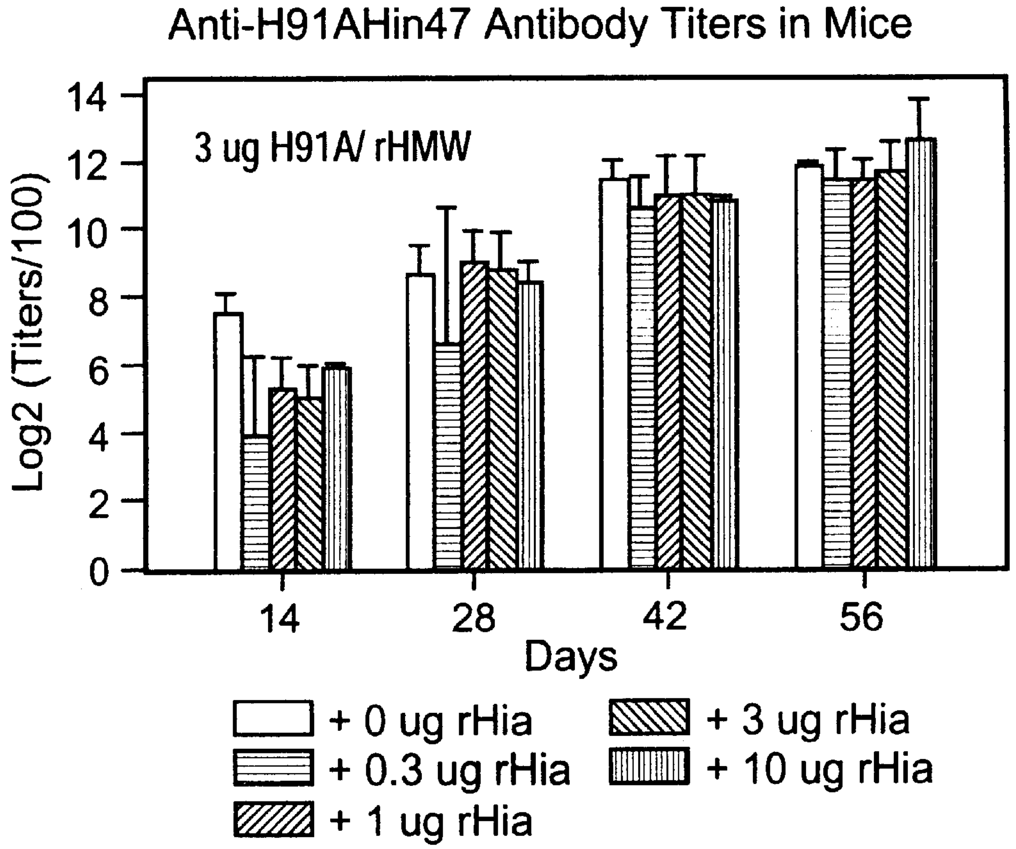
Figure 2A:
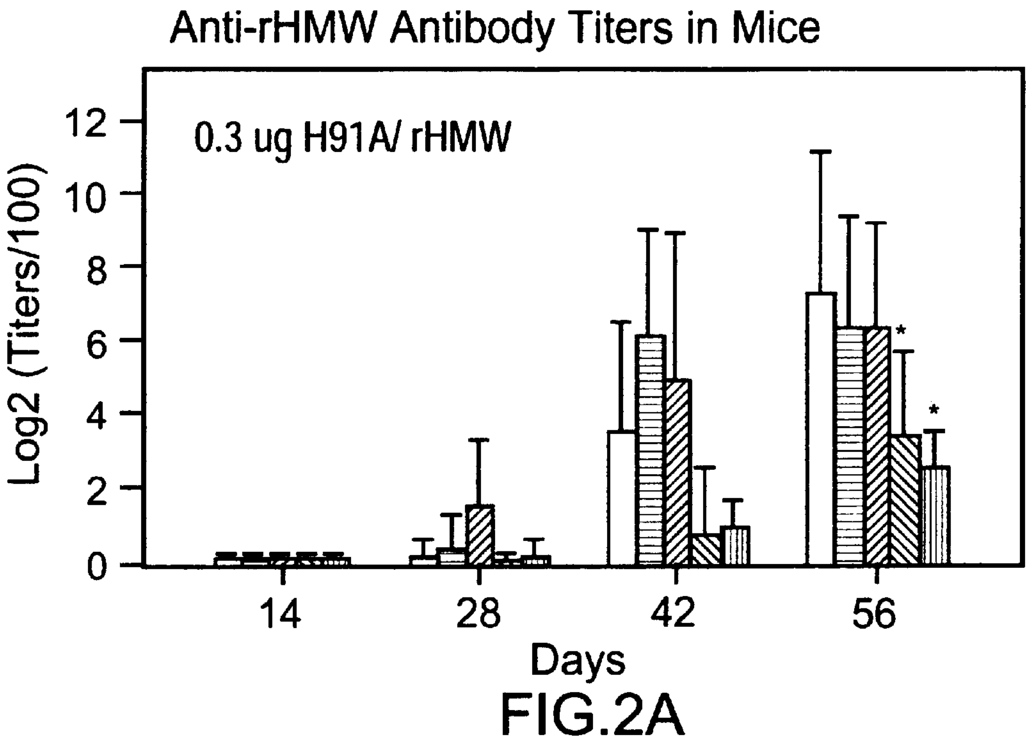
FIG. 2 contain bar graphs A and B, illustrating the anti-HMW immune responses for H91A Hin47+rHMW+rHia combination vaccines in mice. Panel A, 0.3 $\mu$g each of H91A Hin47+rHMW and increasing amounts of rHia. Panel B, 3.0 $\mu$g each of H91A Hin47+rHMW and increasing amounts of rHia. Asterisks indicate statistical significance.
Figure 2B:
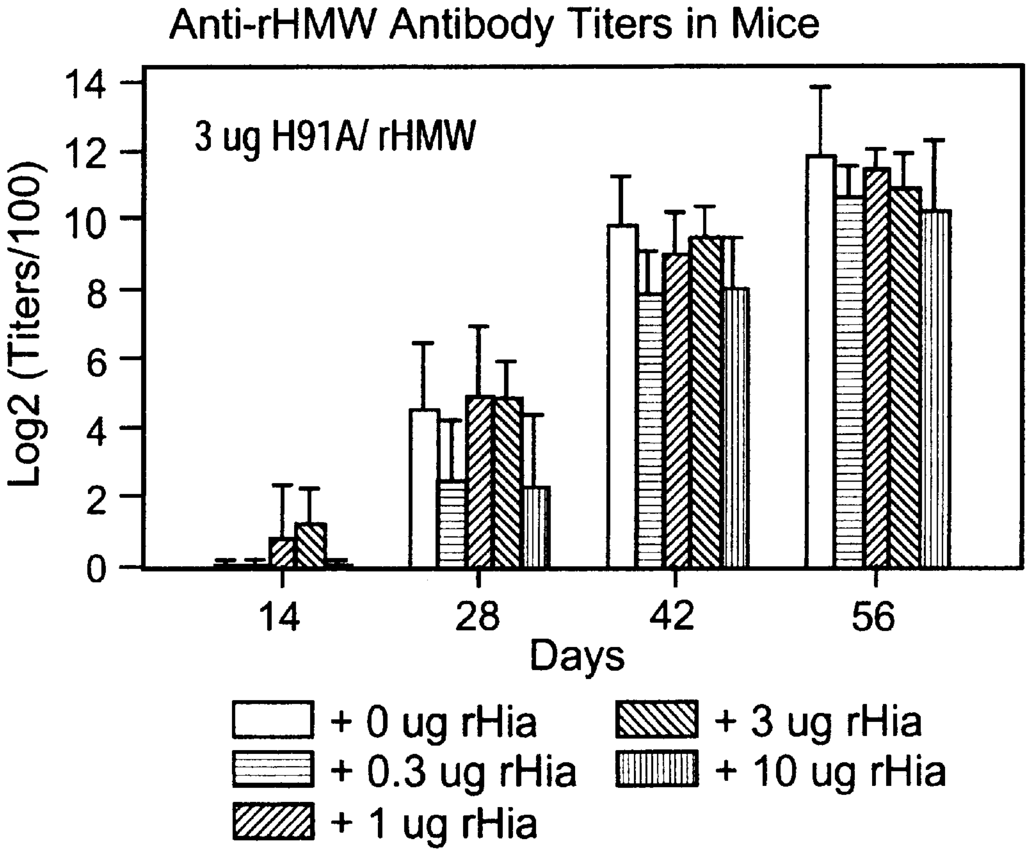
Figure 3A:
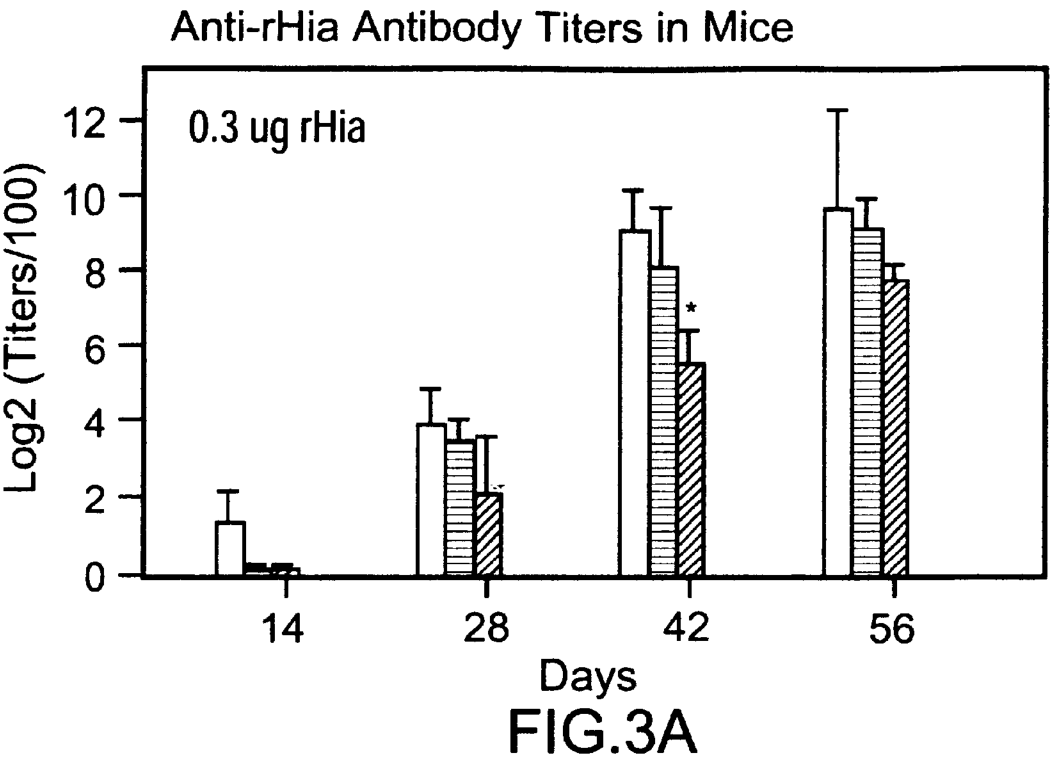
FIG. 3 contains bar graphs A, B, C and D illustrating the anti-Hia immune responses for H91A Hin47+rHMW+rHia combination vaccines in mice. Panel A, 0.3 $\mu$g of rHia and increasing amounts of H91A Hin47+rHMW. Panel B, 1.0 $\mu$g of rHia and increasing amounts of H91A Hin47+rHMW. Panel C, 3.0 $\mu$g of rHia and increasing amounts of H91A Hin47+rHMW. Panel D, 10 $\mu$g of rHia and increasing amounts of H91A Hin47+rHMW. Asterisks indicate statistical significance.
Figure 3B:
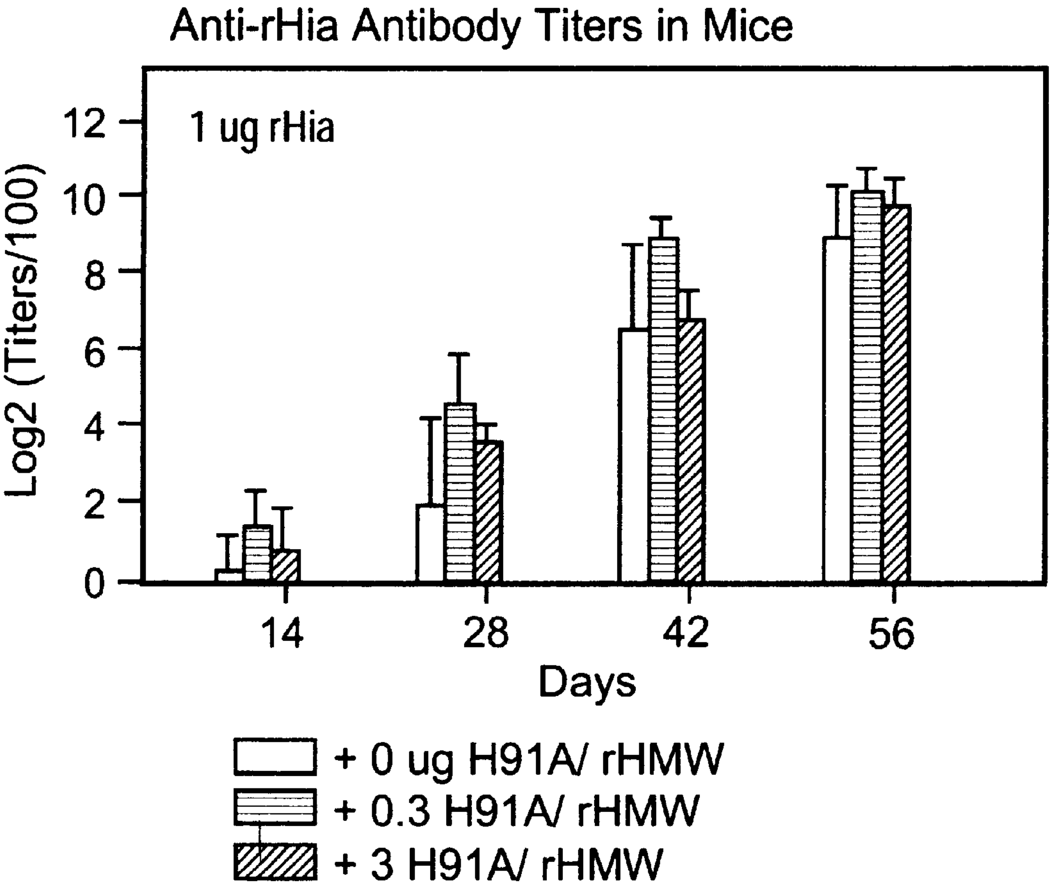
Figure 3C:
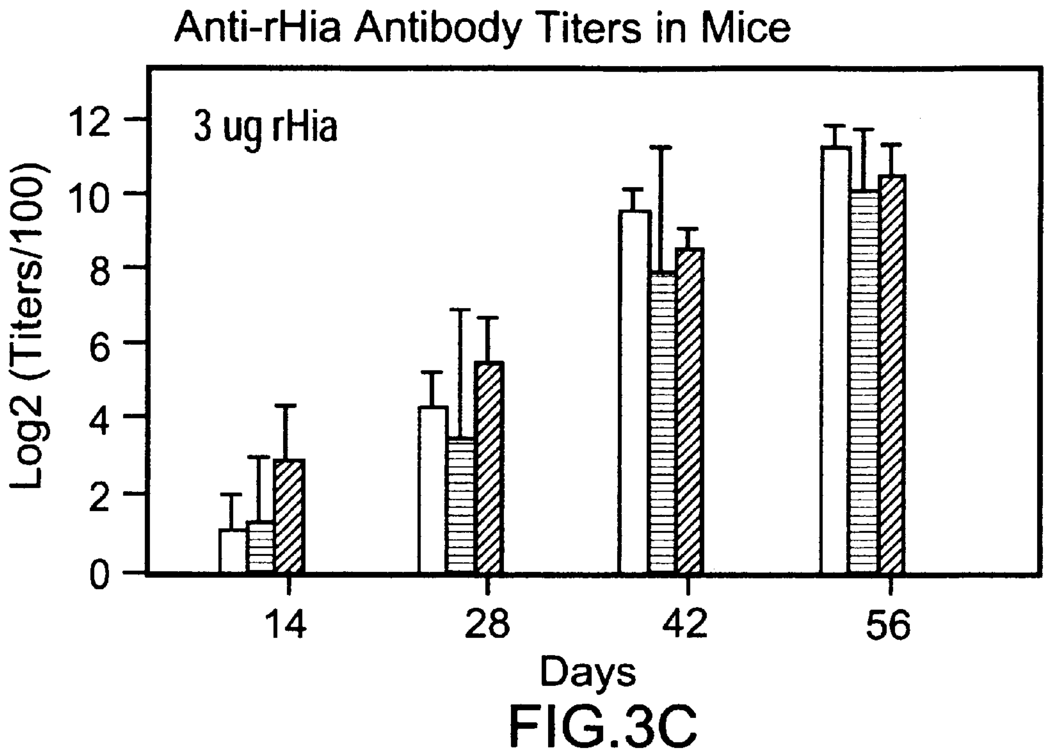
Figure 3D:
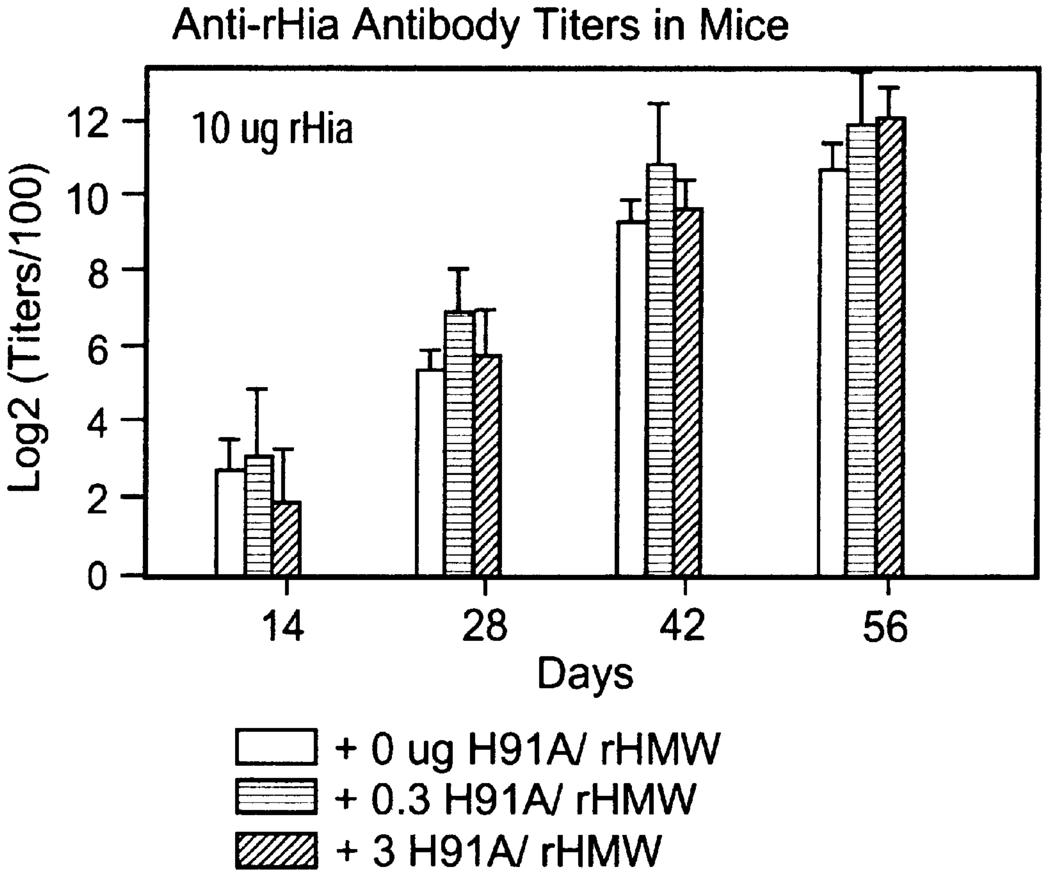

Referring to FIG. 1, there is illustrated the antibody response in mice to the H91A Hin47 antigen of a three-component H91A Hin47+rHMW+rHia vaccine. High antibody titers were achieved with all vaccine combinations at the final bleed. Referring to FIG. 2, there is illustrated the antibody response in mice to the rHMW antigen of a three-component H91A Hin47+rHMW +rHia vaccine. At the 3.0 μg dose of each of H91A Hin47+rHMW, there are high titers of anti-rHMW antibodies found in the final bleed sera irrespective of the amount of rHia in the vaccine composition. However, at the 0.3 μg dose of each of H91A Hin47+rHMW, the anti-rHMW titers are dramatically reduced with increasing amounts of rHia added. Referring to FIG. 3, at the 0.3 μg dose of rHia, there is a suppressive effect on the anti-rHia immune response on day 42 with increasing amounts of H91A Hin47+rHMW. However, this effect is lost by day 56 and is not observed with higher doses, where there is no consequence on the immune response.

Figure 4A:
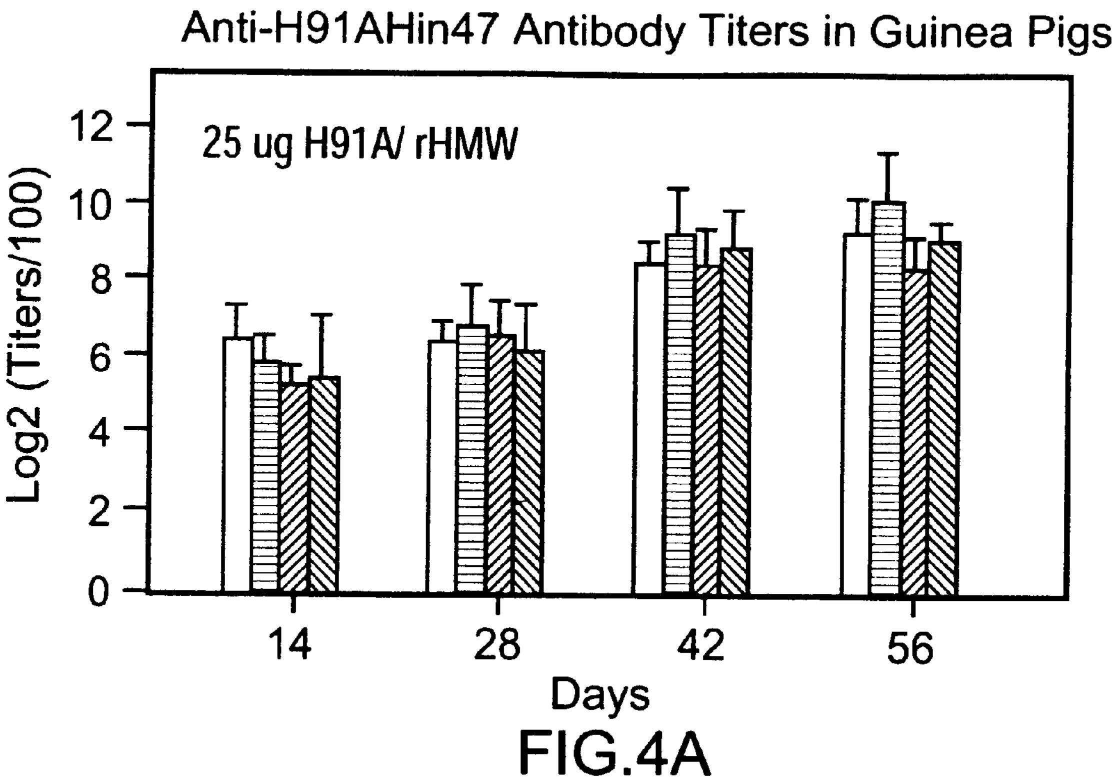
FIG. 4 contains bar graphs A and B, illustrating the anti-H91A Hin47 immune responses for H91A Hin47+rHMW+rHia combination vaccines in guinea pigs—Panel A, 25 $\mu$g each of H91A Hin47+rHMW and increasing amounts of rHia. Panel B, 50 $\mu$g each of H91A Hin47+rHMW and increasing amounts of rHia.
Figure 4B:
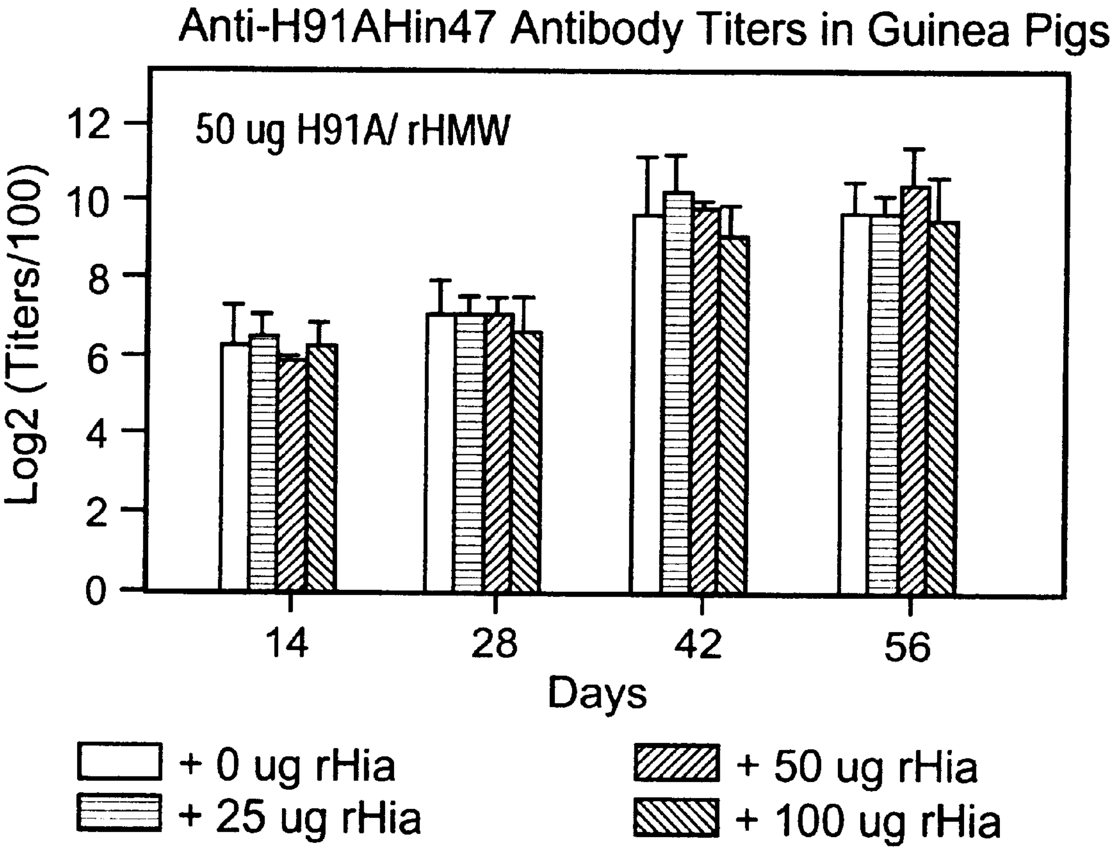
Figure 5A:
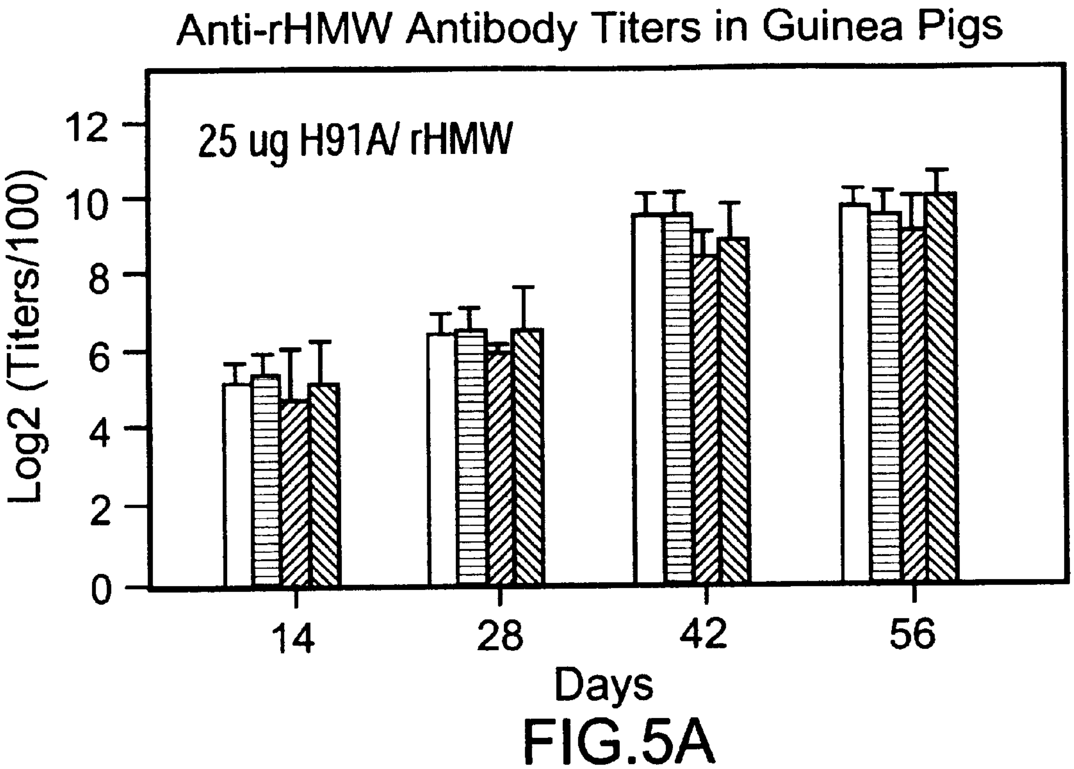
FIG. 5 contains bar graphs A and B, illustrating the anti-HMW immune responses for H91A Hin47+rHMW+rHia combination vaccines in guinea pigs. Panel A, 25 $\mu$g each of H91A Hin47+rHMW and increasing amounts of rHia. Panel B, 50 $\mu$g each of H91A Hin47+rHMW and increasing amounts of rHia.
Figure 5B:
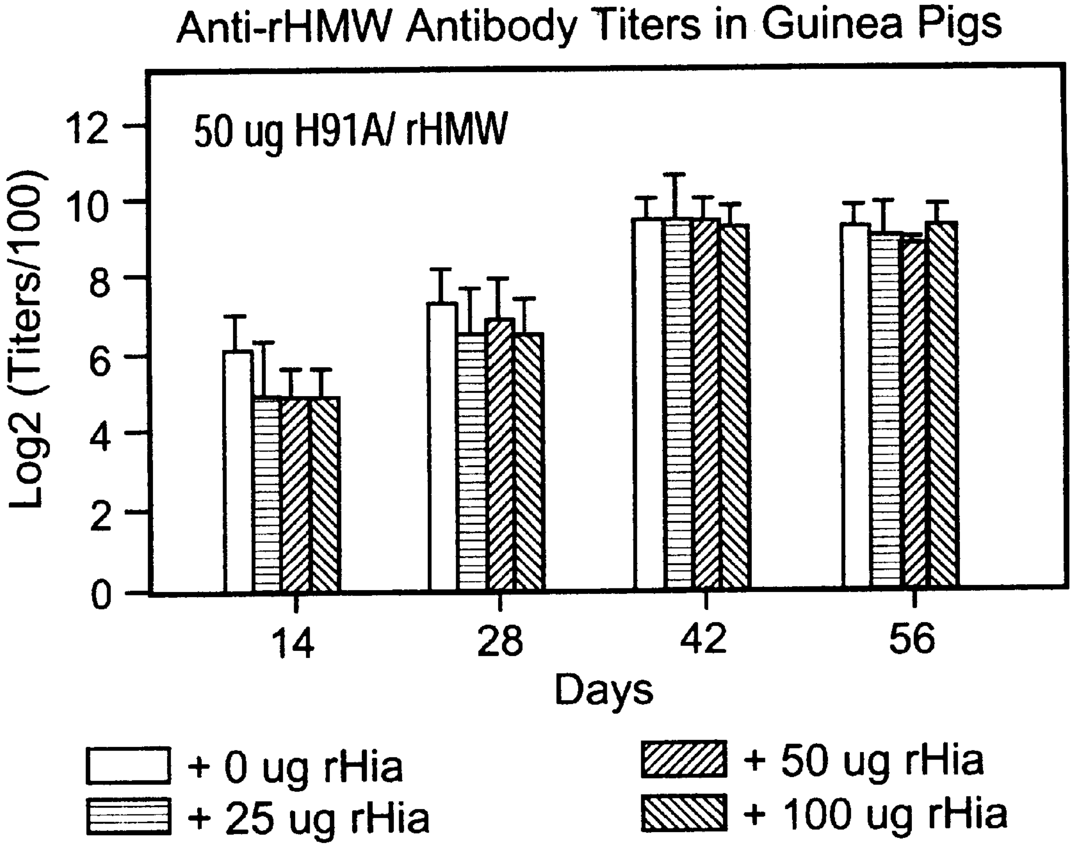
Figure 6A:
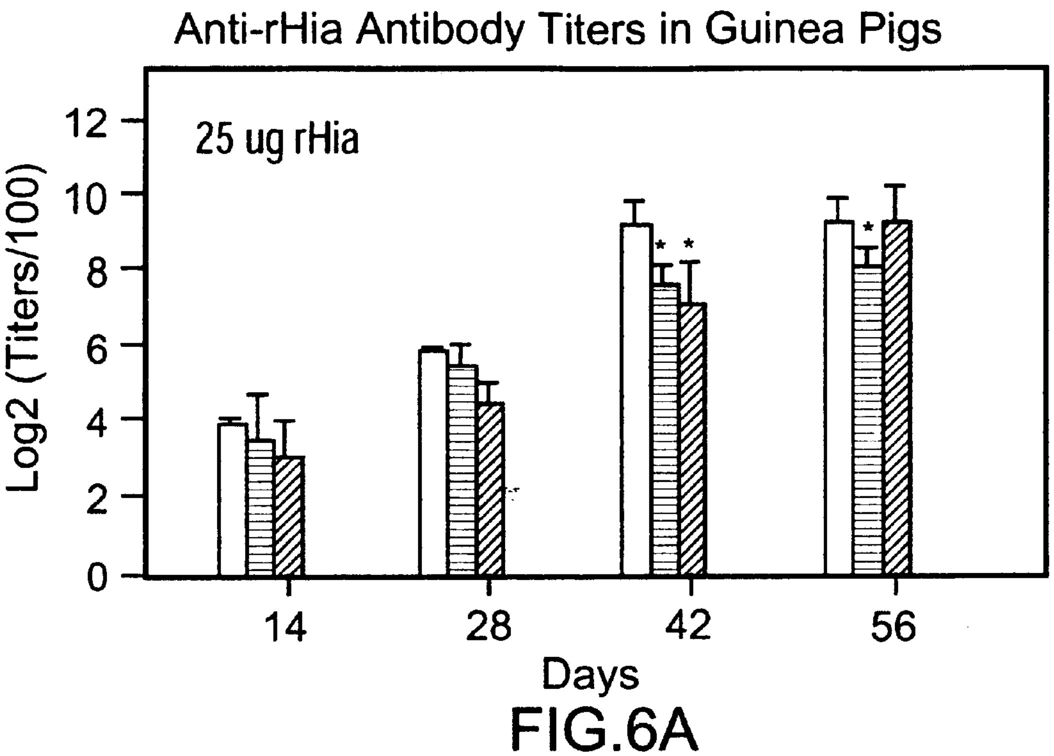
FIG. 6 contains bar graphs A, B and C, illustrating the anti-Hia immune responses for H91A Hin47+rHMW+rHia combination vaccines in guinea pigs. Panel A, 25 $\mu$g of rHia and increasing amounts of H91A Hin47+rHMW. Panel B, 50 $\mu$g of rHia and increasing amounts of H91A Hin47+rHMW. Panel C, 100 $\mu$g of rHia and increasing amounts of H91A Hin47+rHMW. Asterisks indicate statistical significance.
Figure 6B:
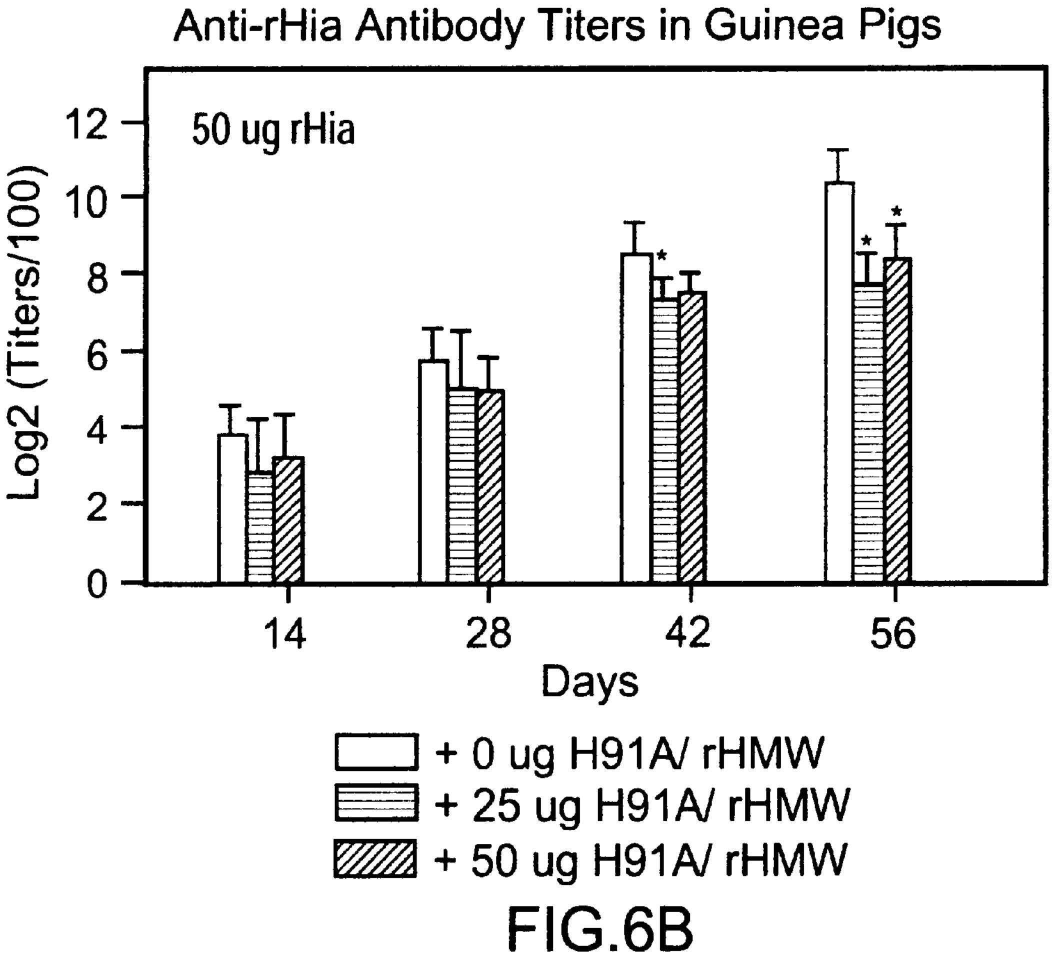
Figure 6C:
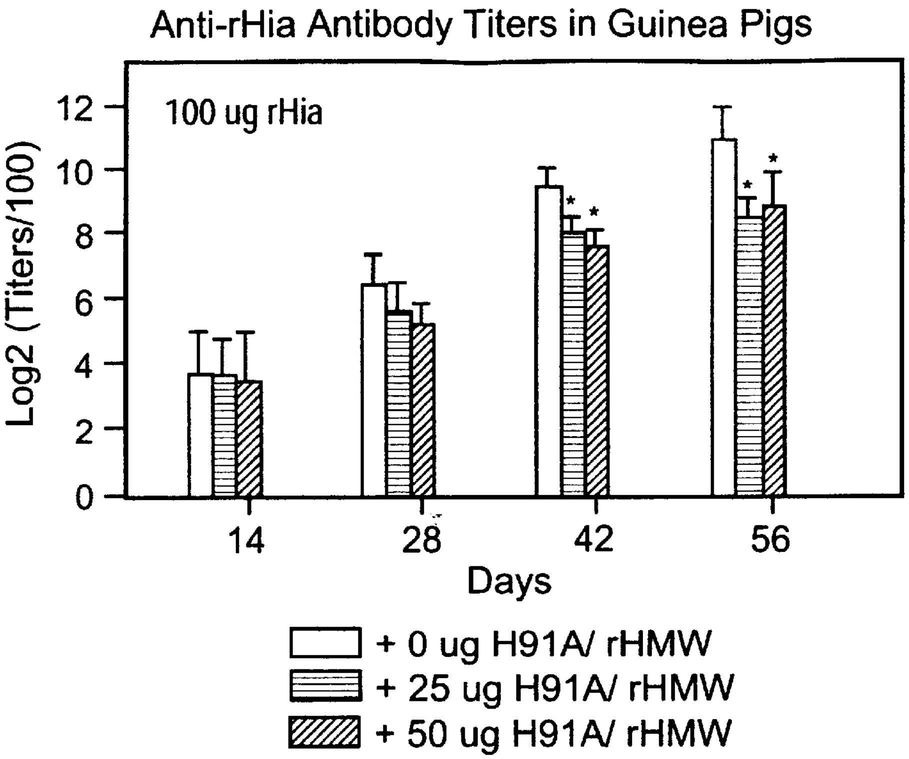

Referring to FIG. 4, there is illustrated the antibody response in guinea pigs to the H91A Hin47 antigen of a three component H91A Hin47+rHMW+rHia vaccine. High antibody titers were achieved with all vaccine combinations at the final bleed and no synergistic or suppressive effects were observed. Referring to FIG. 5, there is illustrated the antibody response in guinea pigs to the rHMW antigen of a three component H91A Hin47+rHMW+rHia vaccine. High antibody titers were achieved with all vaccine combinations at the final bleed and no synergistic or suppressive effects were observed. Referring to FIG. 6, there is illustrated the antibody response in guinea pigs to the rHia antigen of a three component H91A Hin47+rHMW+rHia vaccine. High antibody titers were achieved with all vaccine combinations at the final bleed.

Figure 7:
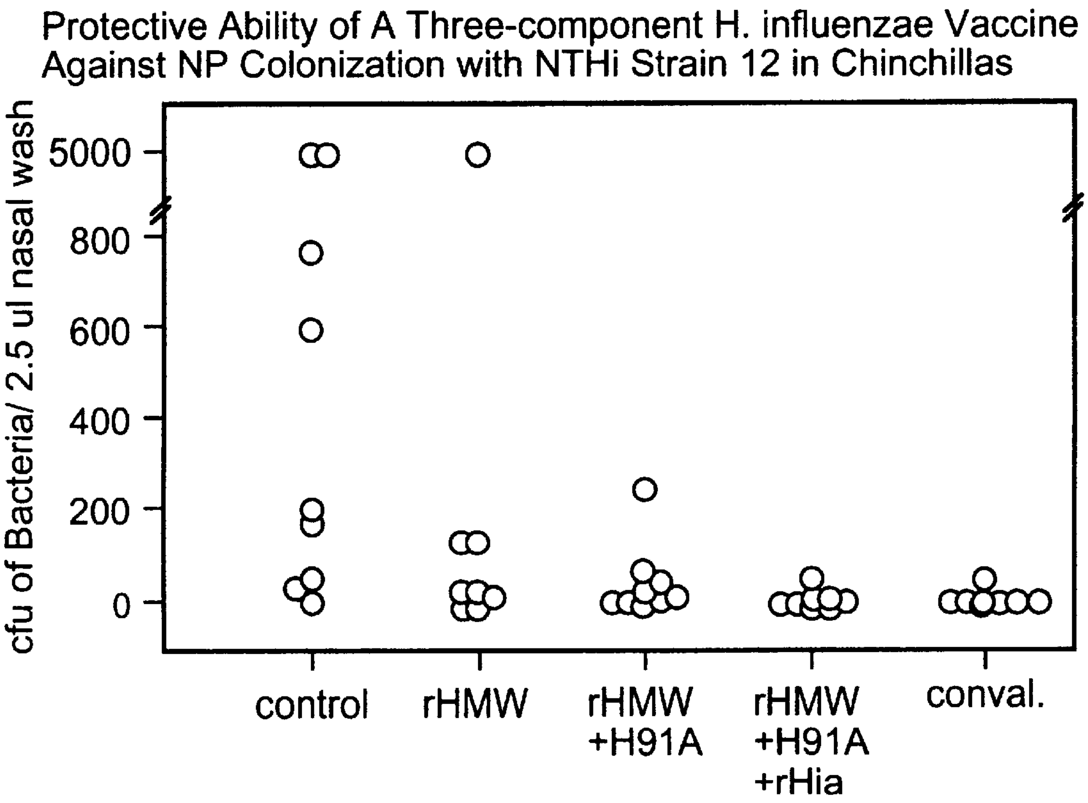
FIG. 7 illustrates the protection of H91A Hin47+rHMW+rHia combination vaccine in the chinchilla model of nasopharyngeal colonization compared to a mono-component or HMW vaccine and a two-component rHMW+H91A Hin47 and convalescent controls.
Figure 8A:
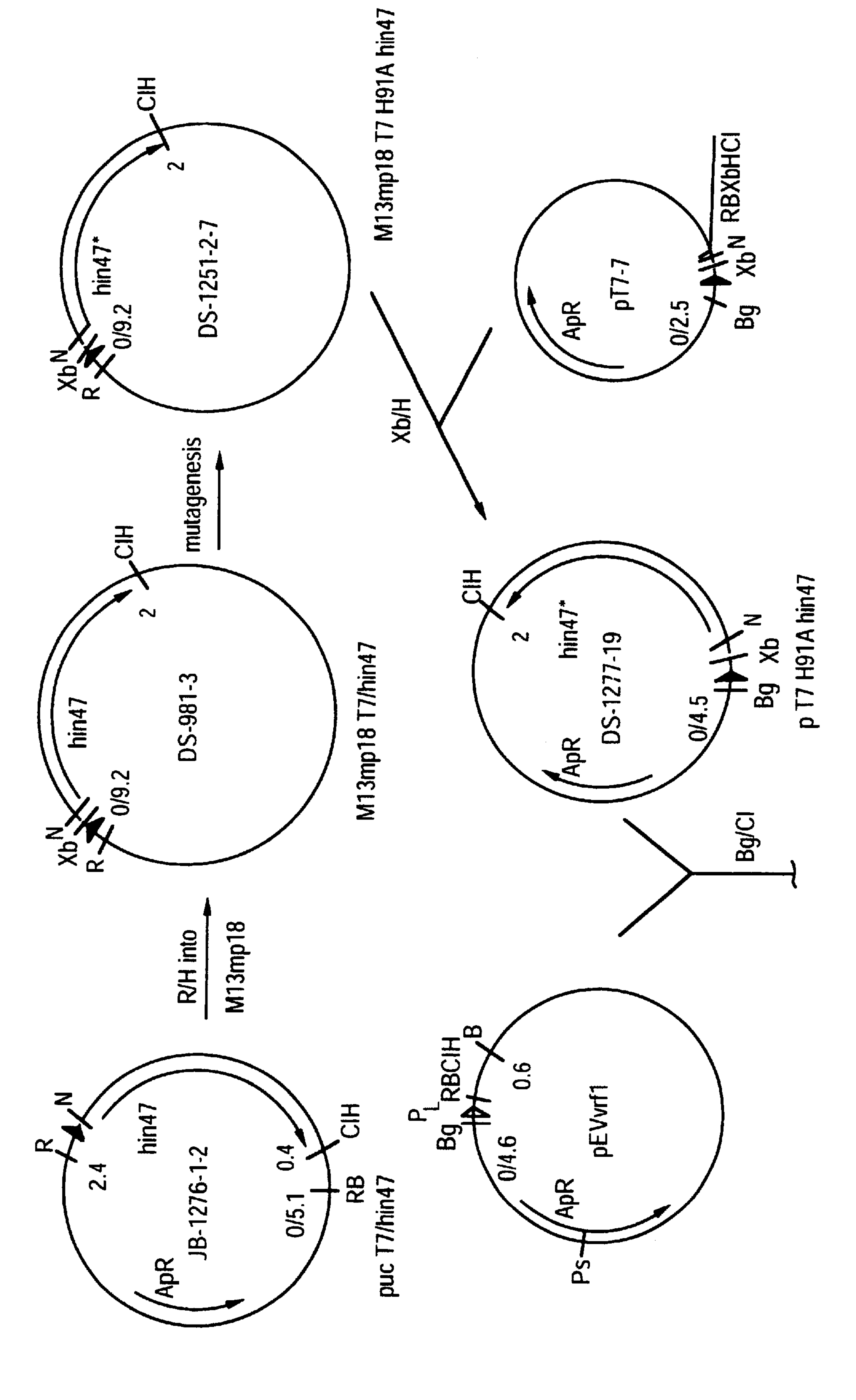
FIG. 8 is a schematic illustration of a construction scheme for producing plasmid DS-2150-1 containing the gene encoding the H91 Hin47 analog.
Figure 8B:
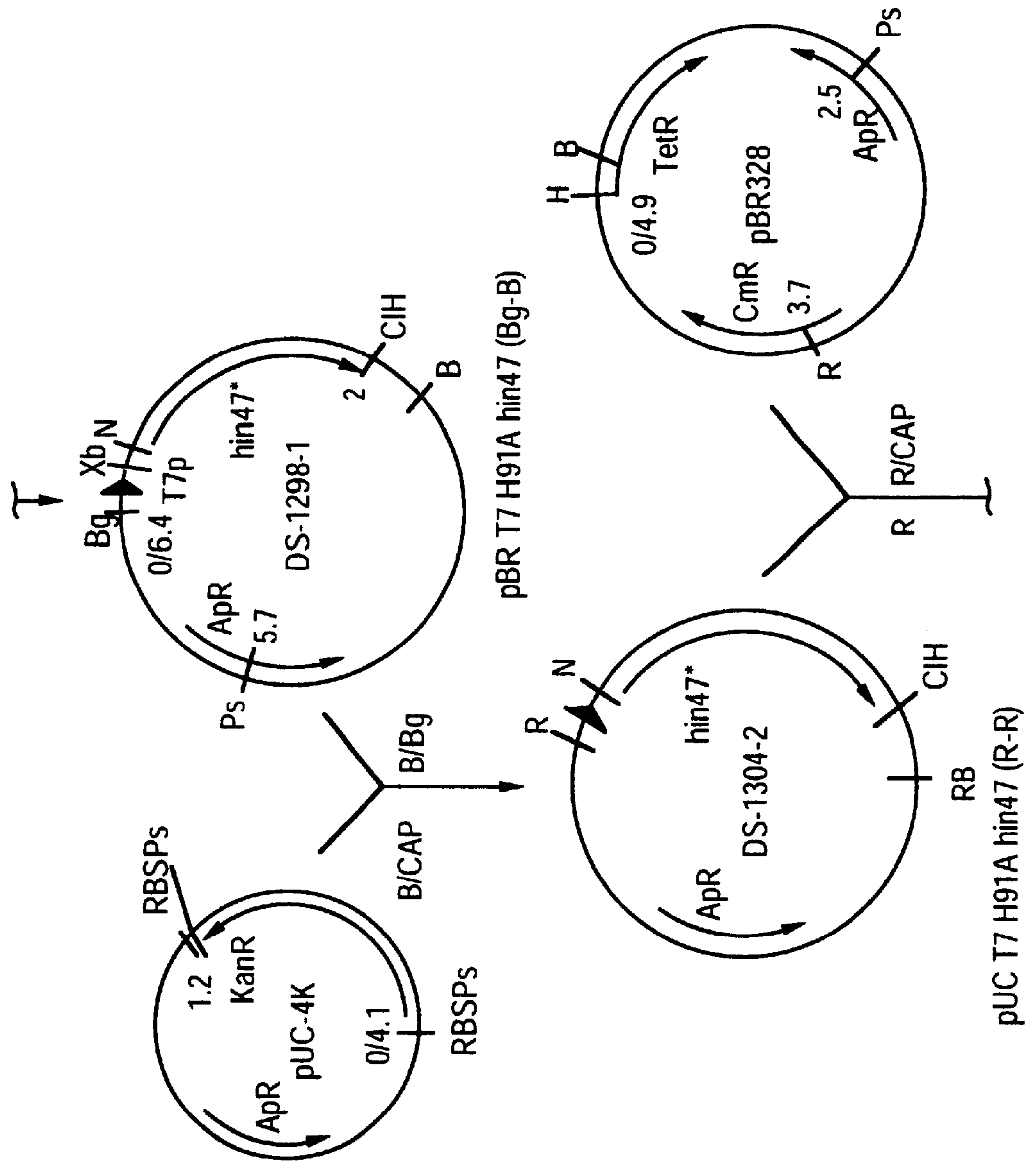
Figure 8C:
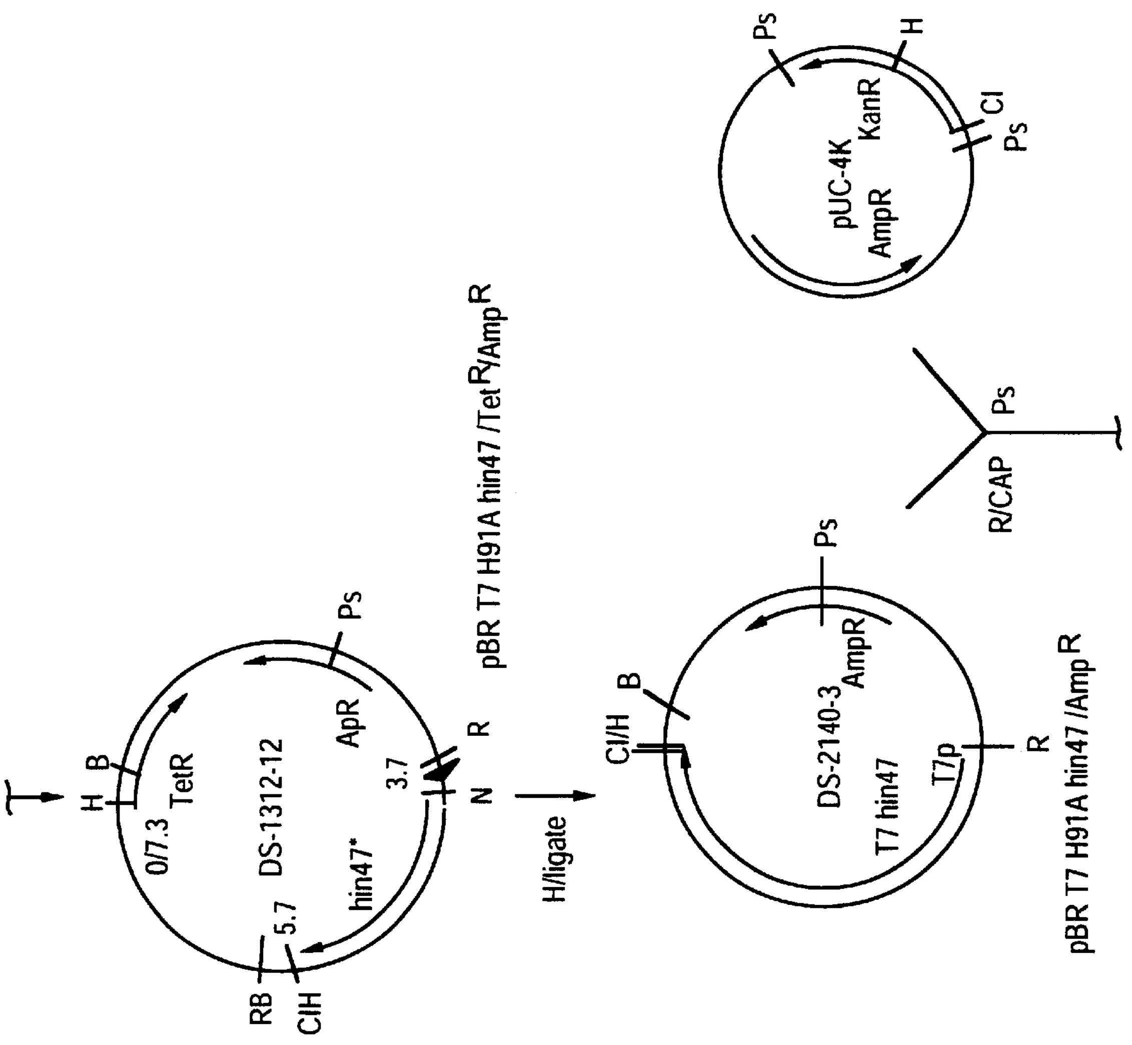
Figure 8D:
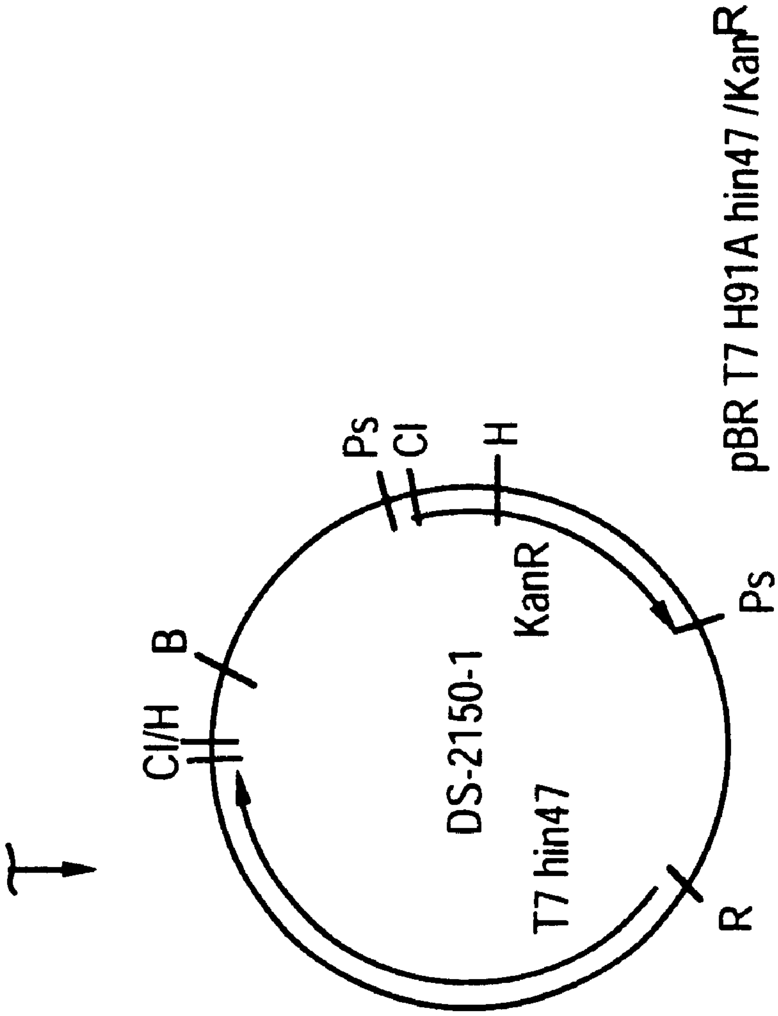

Referring to FIG. 7, there is illustrated the protection afforded by a three-component H91A Hin47+rHMW+rHia vaccine in the nasopharyngeal colonization model compared to the protection afforded by the rHMW component alone or a two component H91A Hin47+rHMW vaccine. The three component vaccine is highly protective, indicating that the addition of more antigens has not effected the protective ability of the rHMW component.

Figure 13:
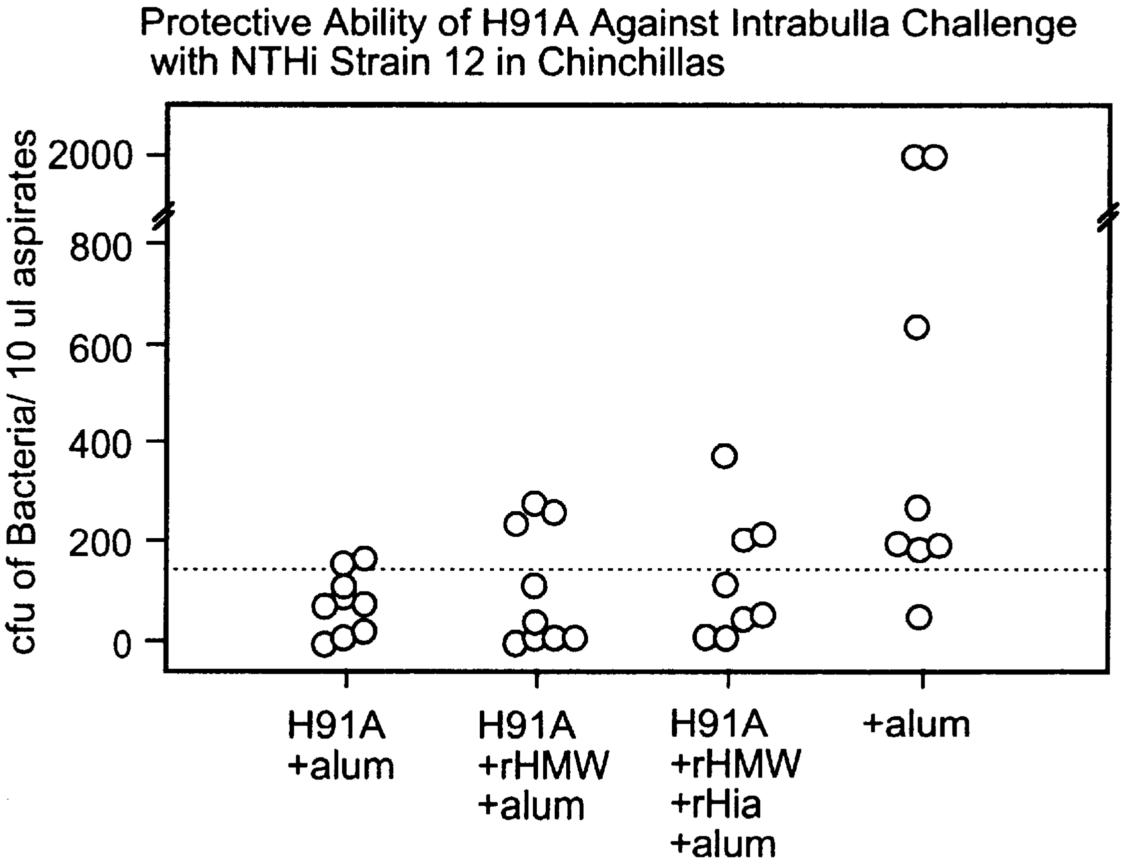
FIG. 13 shows the protection afforded by the H91A Hin47+rHMW rHia combination vaccine in the chinchilla model of intrabulla challenge. The protection afforded by the three-component vaccine is compared to that for a mono-component H91A Hin47 vaccine, a two-component rHMW and H91A Hin47 vaccine are convalescent controls.

Referring to FIG. 13, there is illustrated the protection afforded by the three-component H91A Hin47+rHMW+rHia vaccine against middle ear infection in a chinchilla model. The protection is comparable to that afforded by a monocomponent H91A Hin47 vaccine and a two-component H91A Hin47+rHMW vaccine.

BIOLOGICAL DEPOSITS

Certain vectors that contain nucleic acid coding for a high molecular weight protein of a non-typeable strain of Haemophilus that are described and referred to herein have been deposited with the America Type Culture Collection (ATCC) located at 10801 University Boulevard, Manassas, Va. 20110-2209, USA, pursuant the Budapest Treaty and prior to the filing of this application. Samples of the deposited vectors will become available to the public and all restrictions imposed or access to the deposits will be received upon grant of a patent based on this United States patent application. In addition, the deposit will be replaced if viable samples cannot be dispensed by the Depository. The invention described and claimed herein is not limited in scope by the biological materials deposited, since the deposited embodiment is intended only as an illustration of the invention. Any equivalent or similar vectors that contain nucleic acid which encodes equivalent or similar antigens as described in this application are within the scope of the invention.

Deposit Summary

| Plasmid | ATCC | Deposit Date |
|---|---|---|
| DS-2150-1 | | |
| BK-76-1-1 | 203261 | September 25, 1998 |
| BK-96-2-11 | 203771 | February 11, 1999 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, immunology and fermentation technology used, but not explicitly described in this disclosure and these Examples, are amply reported in the scientific literature and are well within the ability of those skilled in the art.

Example 1

This Example describes the preparation of a H91A Hin47 vaccine component.

A H91A Hin47 mutant was prepared as described in the aforementioned U.S. Pat. No. 5,506,139 and as shown schematically in FIG. 8. Briefly, an oligonucleotide 5'ATCAATAACAGCATTATTGGT3' (SEQ ID NO: 1) was synthesized which can change the Histidine residue at position 91 to an Alanine (ref. 19).

Plasmid JB-1276-1-2 is a pUC-based plasmid containing the T7/hin47 gene on an EcoR I fragment and was used to clone the hin47 gene into M13mp18 for site-directed mutagenesis with the In Vitro Site-Directed Mutagenesis kit from Amersham. The preparation of plasmid JB-1276-1-2 is described in U.S. Pat. No. 5,506,139. The mutation of the His91 codon to Ala91 was confirmed by local sequencing. The H91A mutant hin47 gene was subcloned into pT7-7 to generate plasmid DS-1277-19 (FIG. 8).

The H91A Hin47 expression plasmid (DS-1277-19) utilizes ampicillin selection. The T7/H91A hin47 gene was cloned into pBR328 so that tetracycline selection could be used. Vector DS-1312-12 was thus a pBR328-based plasmid which contained the T7/H91A hin47 gene sequences between EcoR I and Cla I sites, having functional ampicillin and tetracycline resistance genes and containing a repeat of the Hind III-BamH I sequences which are found in both pBR328 and pEVvrfl.

A new plasmid based upon DS-1312-12 was constructed which utilizes kanamycin selection. The construction scheme is shown in FIG. 8. Plasmid DNA from DS-1312-12 was digested with Hind III generating two fragments. The larger 5.9 kb fragment contained a promoterless tetR gene, the ampR gene and the T7/H91A hin47 gene and was re-ligated on itself creating vector DS-2140-3. Plasmid DS-2140-3 was digested with Pst I and the kanR gene from plasmid pUC-4K (P-L Biochemicals) was inserted into the Pst I site, generating plasmid DS-2150-1 which is kanR and sensitive to both ampicillin and tetracycline.

Plasmid DNA from DS-2150-1 was prepared from a 50 mL culture using a protocol based upon the Holmes and Quigley procedure (ref. 21) and including extractions with phenol and chloroform. *E. coli* BL21(DE3) cells were made electrocompetent as follows. Briefly, 10 mL of overnight culture were inoculated into 500 mL of YT medium and the cells were grown at 37° C. with shaking until they reached an $A_{620}$=0.540. The culture was chilled on ice for 30 min., spun at 5 K rpm for 15 min., and the cell pellet resuspended in 500 mL ice cold sterile water. The cell suspension was centrifuged as before and the cell pellet resuspended in 250 mL ice cold sterile water. The cell suspension was spun again, and the cells were resuspended in 10 mL of 10% glycerol. The glycerol suspension was spun, and the cells were resuspended in 1.5 mL of 10% glycerol, aliquotted as 40 $\mu$l samples, and stored at −70° C.

One aliquot of electrocompetent BL21(DE3) cells was thawed on ice and approximately 9 ng of DS-2150-1 DNA was added. Samples were incubated on ice for 3 min. then transferred to a −20° C. BioRad Gene Pulser electrode cuvette and subjected to an electric pulse. 900 $\mu$l of SOC medium were added and the mixture transferred to a culture tube where it was incubated at 37° C. for 1 hour before being plated onto YT agar containing 25 $\mu$g/mL kanamycin. The plate was incubated overnight at 37° C. and single colonies were used for expression studies.

Individual clones were grown in NZCYM medium to an $A_{600\ nm}$ of approximately 0.3 and lactose was added to 1% to induce expression. Cells were grown for 4 hours, then harvested and analysed by SDS PAGE. Clone DS-2171-1-1 was chosen as a representative clone which expressed high levels of H91A Hin47.

The *E. coli* containing DS-2171-1-1 was grown in 2×2 L flasks containing 250 mL of ECGM (containing 8 g/L glucose, pH 6.5) and incubated by shaking at 37° C. for approximately 9 hours in the dark at 250 rpm. The culture fluid (2×250 mL) was inoculated into a 10 L fermentor and the culture grown at 37° C. After approximately 10 hours of incubation, 1% lactose (final concentration) is added for induction, followed by an additional 4 hours incubation.

The culture fluid was harvested into sterile transfer bottles and concentrated and diafiltered by cross-flow filtration against 50 mM Tris/HCI buffer, pH 8.0. The cells in the concentrate are lysed using a high-pressure homogenizer (2 passes at 15,000 psi) to release the H91A Hin47 protein. The cell debris was removed by centrifugation at 15,000 rpm for 1.5 hours. The supernatant was further clarified by centrifugation and filtered through a 0.22 $\mu$m dead-end filter. Products may be stored frozen at −70° C. until further processing.

Sodium chloride (NaCl) was added to the clarified sample to a final concentration of 100 mM. The sample was then purified on an anion exchange chromatography column (TMAE-Fractogel) equilibrated with 50 mM Tris pH 8.0 containing 100 mM NaCl. The H91A Hin47 protein was obtained in the run-through.

The aqueous layer was loaded onto a ceramic hydroxyapatite type 1 (CHTP-1) column equilibrated with 10 mM sodium phosphate buffer pH 8.0. The column was then washed with 150 mM sodium phosphate buffer pH 8.0 and H91A Hin47 was eluted with 175 mM sodium phosphate buffer, pH 8.0 containing 1 M NaCl.

The H91A Hin47 purified protein was concentrated using a 10 kDa molecular weight cut-off membrane followed by diafiltration with approximately 10 volumes of phosphate buffered saline (PBS), pH 7.5.

The H91A Hin47 purified protein in PBS was passed through a Q600 Sartobind membrane adsorber. After passing the solution, the membrane was regenerated using 1.0 M KCl/1.0 M NaOH followed by washing with 1 M KCl then equilibrating with PBS. The process was repeated twice. The concentrated diafiltered H91A Hin47 protein was sterile filtered through a 0.22 $\mu$m membrane filter. Sterile H91A Hin47 protein was adjuvanted with aluminum phosphate. The adosrbed purified concentrate was diluted to produce the adsorbed bulk at 100 $\mu$g/mL.

The concentration of the H91A Hin47 vaccine component was adjusted to 400 $\mu$g $ml^{-1}$ in PBS (pH 7.3) and was adjuvanted with aluminum phosphate to a final concentration of 3 mg $ml^{-1}$. Different doses were prepared by diluting the stock with 3 mg $ml^{-1}$ of aluminum phosphate in PBS.

Example 2

This Example describes the preparation of a rHMW vaccine component.

The production and purification of the rHMW protein has been described in the aforementioned copending U.S. patent application Ser. No. 09/167,568 filed Oct. 7, 1998 and is shown schematically in FIG. 9.

Figure 9A:
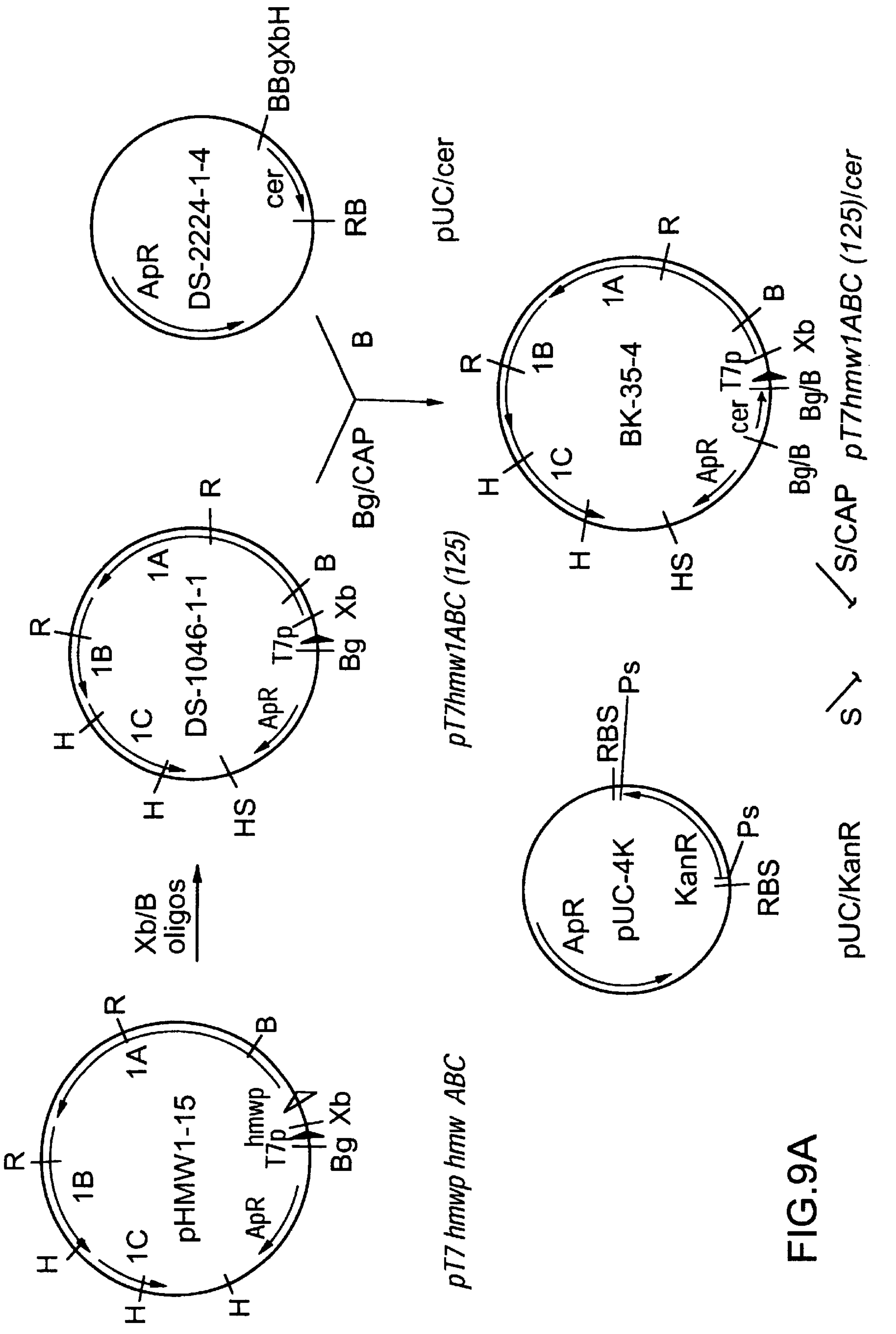
FIG. 9 is a schematic illustration of a construction scheme for producing plasmid BK-76-1-1 containing the hmw1ABC gene cluster from NTHi strain 12.
Figure 9B:
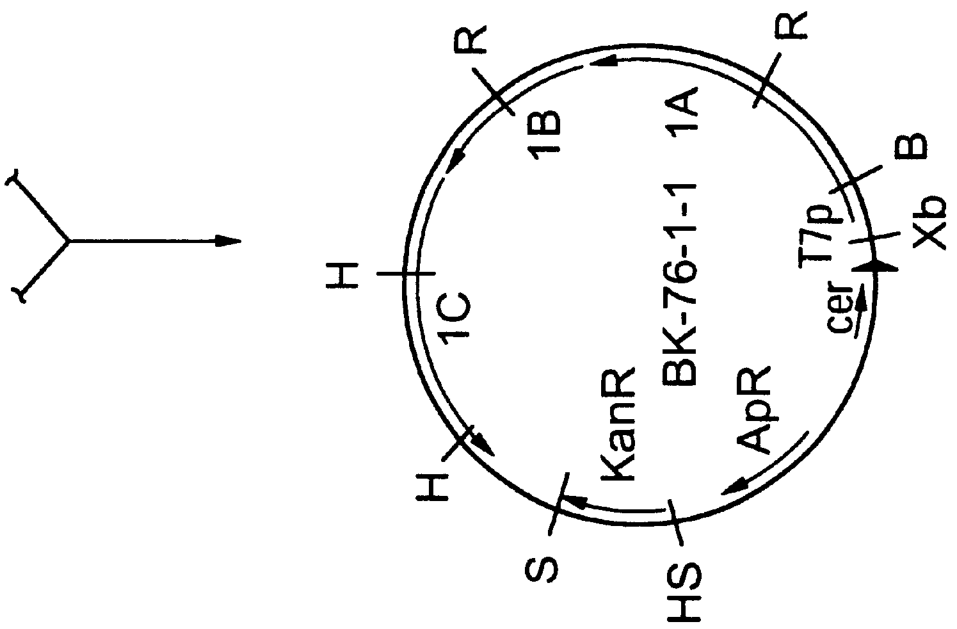

Briefly, plasmid pHMW1-15 (ref. 13) contains a Xba I site within the T7 promoter sequence and a unique BamH I site within the coding sequence of the mature HMW1A protein of non-typeable Haemophilus strain 12. The 1.8 kb Xba I-BamH I fragment of pHMW1-15 was deleted and replaced by an approximately 114 bp Xba I-BamH I fragment generated from oligonucleotides. The resultant 11.3 kb plasmid, DS-1046-1-1, thus contains the T7 promoter joined in frame with the hmw1ABC operon that encodes the mature 125 kDa HMW1A protein (FIG. 9).

Plasmid DS-1046-1-1 contains the T7 hmw1ABC gene cassette and has a unique Bgl II site outside the coding region of the mature HMW1A gene. Plasmid DS-2224-1-4 contains the *E. coli* cer gene located on a BamH I fragment. This fragment was isolated and ligated into the Bgl II site of plasmid DS-1046-1-1 to produce plasmid BK-35-4 (FIG. 9). The kanamycin resistance cassette was excised from pUC 4K by Sal I restriction and ligated into the Sal I restricted BK-35-4 plasmid to produce plasmid BK-76-1-1.

Plasmids were introduced into *E. coli* BL21(DE3) cells by electroporation using a BioRad apparatus. Strains were grown at 37° C. in NZCYM medium to an optical density of $A_{578}$=0.3, then induced by the addition of lactose to 1.0% for 4 hours. Samples were adjusted to 0.2 OD/$\mu$l with SDS-PAGE lysis+loading buffer and the same amount of protein sample was loaded onto SDS-PAGE gels. Clone BK-116-1-1 was selected as a representative clone for preparation of seed stocks.

Recombinant HMW protein was expressed as inclusion bodies in *E. coli*, and were purified by the same procedure (FIG. 12) *E. coli* cell pellets from 500 ml culture were resuspended in 50 ml of 50 mM Tris-HCl, pH 8.0, containing 0.1 M NaCl, and disrupted by sonication. The extract was centrifuged at 20,000 g for 30 min and the resultant supernatant was discarded. The pellet was further extracted, in 50 ml of 50 mM Tris-HCl, pH 8.0 containing 0.5% Triton X-100 and 10 m/M EDTA, then centrifuged at 20,000 g for 30 min, and the supernatant was discarded. The pellet was further extracted in 50 ml of 50 mM Tris-HCl, pH 8.0, containing 1% octylglucoside, then centrifuged at 20,000 g for 30 min, and the supernatant was discarded.

The resultant pellet, obtained after the above extractions, contains the inclusion bodies. The pellet was solubilized in 6 ml of 50 mM Tris-HCl, pH 8.0, containing 6 M guanidine and 5 mM DTT. Twelve ml of 50 mM Tris-HCl, pH 8.0 was added to this solution and the mixture was centrifuged at 20,000 g for 30 min. The supernatant was precipitated with polyethylene glycol (PEG) 4000 at a final concentration of 7%. The resultant pellet was removed by centrifugation at 20,000 g for 30 min and the supernatant was precipitated by $(NH_4)_2SO_4$ at 50% saturation. After the addition of $(NH_4)_2SO_4$, the solution underwent phase separation with protein going to the upper phase, which was then subjected to centrifugation at 20,000 g for 30 min. The resultant pellet was dissolved in 2 ml of 50 mM Tris-HCl, pH 8.0, containing 6 M guanidine HCl and 5 mM DTT and the clear solution was purified on a Superdex 200 gel filtration column equilibrated in 50 mM Tris-HCl, pH 8.0, containing 2 M guanidine HCl. The fractions were analysed by SDS-PAGE and those containing the purified rHMW1 were pooled and dialysed overnight at 4° C. against PBS, then centrifuged at 20,000 g for 30 min. The protein remained soluble under these conditions and glycerol was added to the rHMW1 preparation at a final concentration of 20% for storage at −20° C.

The concentration of the rHMW vaccine component was adjusted to 400 $\mu$g $ml^{-1}$ in PBS (pH 7.3) and was adjuvanted with aluminum phosphate to a final concentration of 3 mg $ml^{-1}$ . Different doses were prepared by diluting the stock with 3 mg $ml^{-1}$ aluminum phosphate in PBS.

Example 3

This Example illustrates the preparation of a rHia vaccine component.

The production and purification of the rHia protein has been described in the aforementioned copending U.S. patent application Ser. No. 09/268,347 filed Mar. 16, 1999 and is shown schematically in FIG. 10.

Figure 10A:
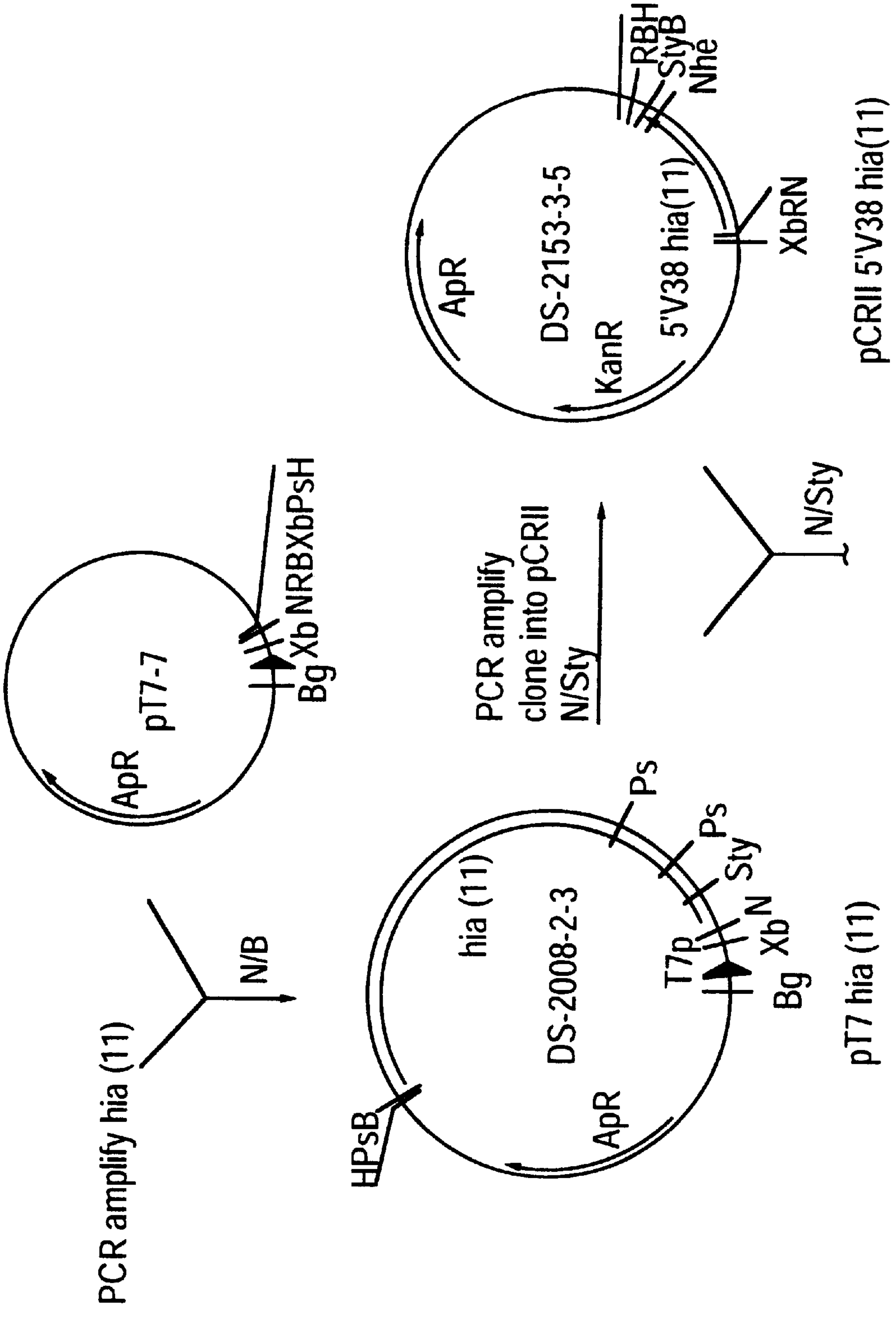
FIG. 10 is a schematic illustration of a construction scheme for producing plasmid BK-96-2-11 containing the gene encoding N-truncated V38 Hia from NTHi strain 11.
Figure 10B:
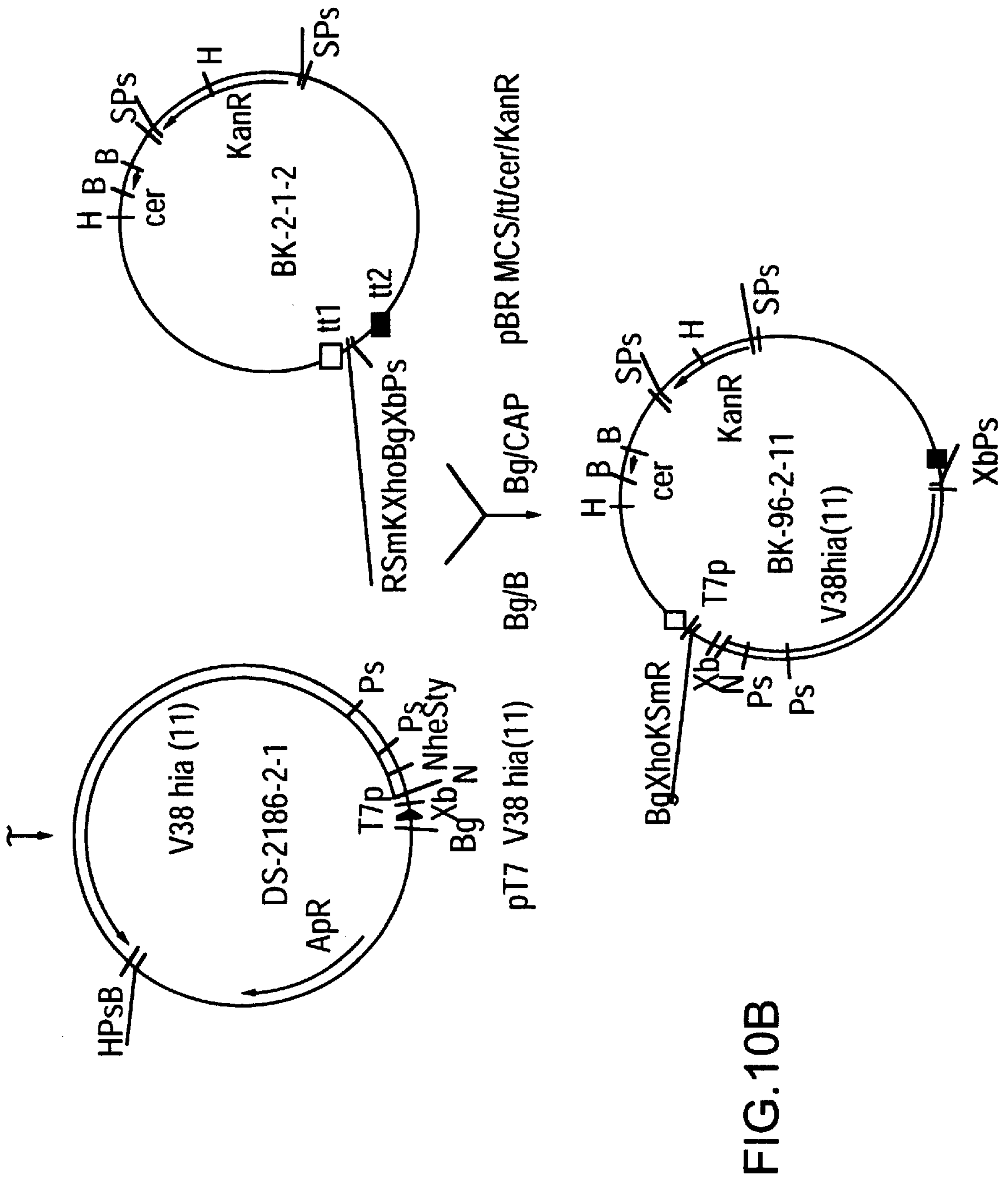

Briefly, chromosomal DNA was purified from NTHi strain 11 and the full-length hia gene was PCR amplified using the oligonucleotides (5038.SL and 5039.SL) (FIG. 11). The PCR product contained an NdeI site at the 5' end and a BamHI dite a the 3' end. This fragment was cloned into the NdeI/BamHI restricted pT7-7 expression vector (ref. 20)producing plasmid DS-2008-2-3 (FIG. 10).

PCR primers (5526.SL and 5528.SL) (FIG. 12) were used to amplify a truncated hia gene fragment from the V38 site to the Sty I site of plasmid DS-2008-2-3, the resulting fragment was TA cloned into plasmid pCRII (Invitrogen) to produce plasmid DS-2153-3-5. This plasmid was then restricted with Nde I and Sty I and this fragment was ligated to the Nde I/Sty I 5.7 kb isolated vector fragment from DS-2008-2-3 to produce plasmid DS-2186-2-1.

Plasmid DS-2186-2-1 containing the V38 truncated hia gene, was restricted with Bgl II and BamH I to release the rHia gene. This fragment was isolated and cloned into the BglII restricted, CAP treated, plasmid BK-2-1-2, to produce plasmid BK 96-2-11. This plasmid now possesses a kanamycin resistance marker and the *E. coli* cer gene as well as the truncated V38 strain 11 hia gene.

The concentration of the rHia vaccine component was adjusted to 400 $\mu$g ml$^{-1}$ in PBS (pH 7.3) and was adjuvanted with aluminum phosphate to a final concentration of 3 mg ml$^{-1}$. Different doses were prepared by diluting the stock with 3 mg ml$^{31\ 1}$ aluminum phosphate in PBS.

Example 4

This Example describes the combination of H91A Hin47+rHMW+rHia as a three-component vaccine.

The preparation of a two-component vaccine comprising H91A Hin47+rHMW, has been described in the aforementioned copending U.S. patent application Ser. No. 09/210,995 filed Dec. 15, 1998. Briefly, vaccines were prepared that comprised combination of H91A Hin47 and rHMW by combining components on day 0, mixing overnight at 4° C. and aliquotted on day 1. The combined vaccines were stored at 4° C. throughout the immunization period.

Vaccines were prepared that comprised the following combinations of rHia with the two component vaccine contained in Table II:

TABLE II

| rHia → 2 COMPONENT ↓ | 0 | 0.3 | 1.0 | 3.0 | 10 | 25 | 50 | 100 |
|---|---|---|---|---|---|---|---|---|
| 0 | | m | m | m | m | gp | gp | gp |
| 0.3 + 0.3 | m | m | m | m | m | | | |
| 3.0 + 3.0 | m | m | m | m | m | | | |
| 25 + 25 | gp | | | | | gp | gp | gp |
| 50 + 50 | gp | | | | | gp | gp | gp |

Notes: 2 component refers to H91A Hin47+rHMW m indicates the vaccine was used to immunize mice. gp indicates that the vaccine was used to immunize guinea pigs.

Vaccine components were combined on day 0, mixed overnight at 4° C., and aliquotted on day 1. The multi-component vaccines were stored at 4° C. throughout the immunization period.

Example 5

This Example describes the analysis of the immunogenicity of the multi-component vaccines in animals.

The immunogenicity of a two-component vaccine comprising H91A Hin47+rHMW, has been described in the aforementioned copending U.S. patent application Ser. No. 09/210,995 filed Dec. 15, 1998.

Groups of five BALB/c mice (Charles River, Quebec) were immunized subcutaneously (s.c.) on days 1, 29 and 43 with one of the mouse vaccines described in Example 4. Blood samples were taken on days 0, 14, 28, 42, and 56.

Groups of five Hartley outbred guinea pigs (Charles River, Quebec) were immunized intramuscularly (i.m.) on days 1, 29 and 43 with one of the guinea pig vaccines described in Example 4. Blood samples were taken on days 0, 14, 28, 42, and 56.

Anti-H91A Hin47, anti-rHMW, and anti-rHia IgG antibody titers were determined by antigen specific enzyme linked immunosorbent assays (ELISAs). Microtiter wells (Nunc-MAXISORB, Nunc, Denmark) were coated with 50 $\mu$l of protein solution (0.4 $\mu$g ml$^{-1}$ for H91A Hin47, 0.4 $\mu$g ml$^{-1}$ for rHMW, or 0.4 $\mu$g ml$^{-1}$ for rHia). The secondary antibodies used were affinity-purified F(ab')$_2$ fragments of goat anti-mouse IgG (Fc-specific) or anti-guinea pig IgG (Fc-specific) antibodies conjugated to horseradish peroxidase (Jackson ImmunoResearch Labs, Mississauga, Ontario). The reactions were developed using tetramethylbenzidine (TMB/H202, ADI, Mississauga, Ontario) and absorbancies were measured at 450 nm (using 540 nm as a reference wavelength) in a Flow Multiskan MCC microplate reader (ICN Biomedicals, Mississauga, Ontario). The reactive titer of an antiserum was defined as the reciprocal of the dilution consistently showing a two-fold increase in adsorbance over that obtained with the prebleed serum sample.

The results of the immunogenicity studies are illustrated in FIGS. 1 to 6. As shown in FIG. 1, the final bleed sera obtained from mice immunized with 0.3 $\mu$g each of H91A Hin47+rHMW or with 3.0 $\mu$g each of H91A Hin47+rHMW and 0, 0.3, 1.0, 3.0 or 10 $\mu$g of rHia all had equivalent high antibody titers to H91A Hin47. These data show that there is neither a synergistic nor an interfering affect on the anti-H91A Hin47 antibody titer with added rHia.

As shown in FIG. 2, panel A, the final bleed sera obtained from mice immunized with 0.3 $\mu$g each of H91A Hin47+rHMW and 0, 0.3, 1.0, 3.0 or 10 $\mu$g of rHia had significantly reduced anti-HMW titers with increased amounts of rHia added. These data indicate that at low concentrations of H91A Hin47+rHMW, there is suppression of the anti-HMW antibody response caused by the addition of rHia. When mice are immunized with 3 $\mu$g each of H91A, Hin47+rHMW, and 0, 0.3, 1.0, 3.0 or 10 $\mu$g of rHia, no affect was observed and high titers of anti-rHMW antibodies were obtained in the final bleed sera (FIG. 2, panel B).

As shown in FIG. 3, panel A, the addition of 3.0 $\mu$g each of H91A Hin47+rHMW to 0.3 $\mu$g of rHia, had a transient suppressive effect on the anti-rHia response at day 42, that disappeared by day 56. However, as shown in FIG. 3, panels B to D, there was no suppressive effect observed at higher doses of rHia.

As shown in FIG. 4, panels A and B, the final bleed sera from guinea pigs immunized with 25 $\mu$g each of H91A Hin47+rHMW or 50 $\mu$g each of H91A Hin47+rHMW and 0, 25, 50 or 100 $\mu$g of rHia all had high titers of anti-H91A Hin47 antibodies. These data indicate that there was neither a synergistic nor a suppressive affect on the anti-H91A Hin47 antibody response in the presence of the three antigens.

As shown in FIG. 5, panels A and B, the final bleed sera from guinea pigs immunized with 25 $\mu$g each of H91A Hin47 rHMW or 50 $\mu$g each of H91A Hin47+rHMW and 0, 25, 50 or 100 $\mu$g of rHia all had high titers of anti-rHMW antibodies. These data indicate that there was neither a synergistic nor a suppressive affect on the anti-rHMW antibody response in the presence of the three antigens.

As shown in FIG. 6, panels A to C, the final bleed sera from guinea pigs immunized with 25, 50 or 100 $\mu$g of rHia with or without added H91A Hin47+rHMW, all had high titer anti-rHia antibodies. There was, however, a slight but statistical inhibition of the anti-rHia response after booster doses containing all three antigens.

Example 6

This Example describes the protective ability of a multi-component vaccine in animal models of disease.

In young chinchillas, it has been demonstrated that nasopharyngeal colonization with non-typeable *H. influenzae* leads to otitis media (ref. 14). rHMW is partially protective in a chinchilla nasopharyngeal colonization challenge model, as described in copending U.S. patent application Ser. No. 09/167,568. In this model, animals are immunized i.m. on days 0, 14 and 28 with 25, 50 or 100 μg of rHMW, adsorbed to alum, and challenged on day 44 with $10^8$ cfu of live bacteria delivered intranasally (50 μl per nares).

Nasopharyngeal lavage is performed 4 days post challenge using 1 ml of sterile saline as wash. 25 μl of wash is plated onto chocolate agar in the presence of streptomycin and the plates incubated at 37° C. for 24 h. (The challenge strain was made streptomycin resistant by serial passaging, in order to facilitate the quantitation of recovered bacteria in the presence of natural flora that are killed by the streptomycin.) Convalescent animals or those mock-immunized with alum alone, are used as controls. For the multi-component vaccine study, 50 μg each of rHMW, rHia, and H91A Hin47 were mixed as described in Example 4 and chinchillas were immunized as described above.

The results of the protection study are shown in FIG. 7 which indicates that there is still excellent protection afforded in the nasopharyngeal colonization challenge model by the combination of rHMW+rHia+H91A Hin47.

In addition, as seen in FIG. 13, the three-component vaccine afforded partial protection in the intrabulla challenge model. This model has been described previously (ref. 19). Young chinchillas are immunized i.m. on days 0, 14 and 28 with 50 μg of each of the antigens tested, adsorbed to alum. The chinchillas were then challenged on day 44 with 350 cfu of live organisms delivered into the middle ear space via the epitympanic bulla. Animals are then monitored by tympanometry and middle ear fluid is collected 4 days post-challenge, mixed with 200 μl of BHI medium and dilution plated onto chocolate agar plates that are incubated for 24 hours at 37° C. Convalescent animals or those immunized with alum alone, are used as controls. For the multi-component vaccine study, 50 μl each of H91A Hin47, rHMW and rHia were mixed as described in Example 4.

SUMMARY OF DISCLOSURE

In summary of this disclosure, the present invention provides a multi-component vaccine against *Haemophilus influenzae* having a wide spectrum of efficacy and comprising three different antigens of *Haemophilus influenzae*, two of which different antigens are adhesin. Modifications are possible within the scope of this invention.

REFERENCES

1. Barbour, M. L., R. T. Mayon-White, C. Coles, D. W. M. Crook, and E. R. Moxon. 1995. The impact of conjugate vaccine on carriage of *Haemophilus influenzae* type b. J. Infect. Dis. 171:93–98.
2. Berkowitz et al. 1987. J. Pediatr. 110:509.
3. Claesson et al. 1989. J. Pediatr. 114:97.
4. Black, S. B., H. R. Shinefield, B. Fireman, R. Hiatt, M. Polen, E. Vittinghoff, The Northern California Kaiser Permanent Vaccine Study Center Pediatrics Group. Efficacy in infancy of oligosaccharide conjugate *Haemophilus influenzae* type b (HbOC) vaccine in a United States population of 61,080 children. 1991. Pediatr. Infect. Dis. J. 10:97–104.
5. Nitta, D. M., M. A. Jackson, V. F. Burry, and L. C. Olson. 1995. Invasive *Haemophilus influenzae* type f disease. Pediatr. Infect. Dis J. 14:157–160.
6. Waggoner-Fountain, L. A., J. O. Hendley, E. J. Cody, V. A. Perriello, and L. G. Donowitz. 1995. The emergence of *Haemophilus influenzae* types e and t as significant pathogens. Clin. Infect. Dis. 21:1 122–1324.
7. Madore, D. V. 1996. Impact of immunization on *Haemophilus influenzae* type b disease. Infectious Agents and Disease 5:8–20.
8. Bluestone, C. D. 1982. Current concepts in otolaryngology. Otitis media in children: to treat or not to treat? N. Engl. J. Med. 306:1399–1404.
9. Barenkamp, S. J., and F. F. Bodor. 1990. Development of serum bactericidal activity following nontypable *Haemophilus influenzae* acute otitis media. Pediatr. Infect. Dis. 9:333–339.
10. Barenkamp, S. J., and J. W. St. Geme III. 1994. Genes encoding high-molecular weight adhesion proteins of nontypeable *Haemophilus influenzae* are part of gene clusters. Infect. Immun. 62:3320–3328.
11. St. Geme III, J. W., V. V. Kumar, D. Cutter, and S. J. Barenkamp. 1998. Prevalence and distribution of the hmw and hia genes and the HMW and Hia adhesins among genetically diverse strains of nontypeable *Haemophilus influenzae*. Infect. Immun.66:364–368.
12. St. Geme III, J. W., S. Falkow, and S. J. Barenkamp. 1993. High-molecular-weight proteins of nontypeable *Haemophilus influenzae* mediate attachment to human epithelial cells. Proc. Natl. Acad. Sci. USA 90:2875–2879.
13. Barenkamp, S. J. 1996. Immunization with high-molecular-weight adhesion proteins of nontypeable *Haemophilus influenzae* modifies experimental otitis media in chinchillas. Infect. Immun. 64:1246–1251.
14. Yang, Y. -P., S. M. Loosmore, B. Underdown,, and M. H. Klein. 1998. Nasopharyngeal colonization with nontypeable *H. influenzae* in chinchillas. Infect. Immun. 66:1973–1980.
15. St. Geme, J. W. and D. Cutter. 1995. Evidence that surface fibrils expressed by *Haemophilus influenzae* type b promote attahment to human epithelial cells. Molec. Microbiol. 15:77–85.
16. Barenkamp, S. J. and J. W. St. Geme. 1996. Identification of a second family of high-molecular-weight adhesion proteins expressed by non-typable *Haemophilus influenzae*. Molec. Microbiol. 19:1215–1223.
17. St. Geme, J. W., D. Cutter, and S. J. Barenkamp. 1996. Characterization of the genetic locus encoding *Haemophilus influenzae* type b surface fibrils. J. Bact. 178:6281–6287.
18. Retzlaff, C., Y. Yamamoto, P. S. Hoffman, H. Friedman, and T. W. Klein. 1994. Bacterial heat shock proteins directly induce cytokine mRNA and interleukin-1 secretion in macrophage cultures. Infect. Immun. 62:5689–5693.
19. Loosmore, S. M., Y-P. Yang, R. Oomen, J. Ni. Shortreed, D. C. Coleman, and M. H. Klein. 1998 The *Haemophilus influenzae* HtrA protein is a protective antigen. Infect. Immun. 66:899–906.
20. Tabor, S., and C. C. Richardson. 1985. A bacteriophage T7 RNA polymerase/promoter system for controlled exclusive expression of specific genes. Proc. Natl. Acad. Sci. USA 82:1074–1078.
21. Holmes, D. S. and Quigley, M. 1981. A rapid boiling method for the preparation of bacterial plasmids. Anal. Biochem. 114:193–197.

What we claim is:

1. An immunogenic composition for conferring protection in a host against disease caused by *Haemophilus influenzae*, which comprises:

(a) an isolated and purified analog of *Haemophilus influenzee* Hin47 protein having a decreased protease activity which is less than about 10% of natural Hin47 protein, (b) an isolated and purified *Haemophilus influenzae* adhesin (Hia) protein of a non-typeable strain of *Haemophilus influenzae*, and (c) an isolated and purified high molecular weight (HMW) protein of a non-typeable strain of *Haemophilus influenzae.*

2. The composition of claim 1 wherein said Hin47, Hia and HMW proteins are present in amounts which do not impair the individual immunogenicities of the proteins.

3. The composition of claim 2 wherein said analog of Hin47 protein is one in which at least one amino acid of the natural Hin47 protein contributing to protease activity has been deleted or replaced by a different amino acid and which has substantially the same immunogenic properties as natural Hin47 protein.

4. The composition of claim 3 wherein said at least one amino acid is selected from the group consisting of amino acids 91, 121 and 195 to 201 of natural Hin47 protein.

5. The composition of claim 4 wherein Serine-197 is replaced by alanine.

6. The composition of claim 4 wherein Histidine-91 is replaced by alanine, lysine or arginine.

7. The composition of claim 6 wherein Histidine-91 is replaced alanine.

8. The composition of claim 4 wherein Asp-121 is replaced by alanine.

9. The composition of claim 2 wherein said Hia protein is produced recombinantly.

10. The composition of claim 9 wherein said recombinantly-produced Hia protein is an N-terminal truncation to position 37 and having a valine at position 38 (V38 rHia).

11. The composition of claim 2 wherein said HMW protein is an HMW1 or HMW2 protein of a non-typeable strain of *Haemophilus influenzae.*

12. The composition of claim 11 wherein the HMW1 and HMW2 proteins are produced recombinantly.

13. The composition of claim 11 wherein said HMW1 and HMW2 proteins are isolated from the respective strain of non-typeable *Haemophilus influenzae* and possess respective molecular weights as set forth in the following Table:

| | | Molecular Weight (kDa) non-typeable *H. influenzae* Strain | | | | | |
|---|---|---|---|---|---|---|---|
| | | 11 | JoyC | K21 | LCDC2 | PMH1 | 15 |
| Mature Protein: | HMW1 | 125 | 125.9 | 104.4 | 114.0 | 102.4 | 103.5 |
| | HMW2 | 120 | 100.9 | | 111.7 | 103.9 | 121.9. |

14. The composition of claim 1 further comprising an adjuvant.

15. The composition of claim 14 wherein said adjuvant is aluminum hydroxide or aluminum phosphate.

16. The composition of claim 1 comprising (a) about 25 to about 100 $\mu$g of the Hin47 protein analog, and (b) about 25 to about 100 μg of the Hia protein, and (c) about 25 to about 100 μg of the HMW protein.

17. The composition of claim 1 further comprising at least one additional antigenic component for conferring protection against infection caused by another pathogen.

18. The composition of claim 1 wherein said at least one additional antigenic component is selected from the group consisting of diphtheria toxoid, tetanus toxoid, pertussis antigens, non-virulent poliovirus and PRP-T.

19. The composition of claim 18 wherein said pertussis antigens are selected from the group consisting of pertussis toxoid, filamentous hemagglutinin, pertactin and agglutinogens.

20. A method of immunizing a host against disease caused by infection with *Haemophilus influenzae*, including otitis media, which comprises administering to the host an immunoeffective amount of a composition as claimed in claim 1.

* * * * *